United States Patent
Telser et al.

(10) Patent No.: US 12,337,053 B2
(45) Date of Patent: Jun. 24, 2025

(54) METHOD AND COMPOSITION FOR COLORING A KERATINOUS SUBSTRATE USING SOLUBILIZED VAT DYES

(71) Applicant: Wella Germany GmbH, Darmstadt (DE)

(72) Inventors: Sonja Telser, Heidelberg (DE); Ingo Weber, Basel (CH); Petra Braun, Munster (DE); Markus Speckbacher, Mettenheim-Hart (DE)

(73) Assignee: WELLA GERMANY GMBH, Darmstadt (DE)

( * ) Notice: Subject to any disclaimer, the term of this patent is extended or adjusted under 35 U.S.C. 154(b) by 152 days.

(21) Appl. No.: 18/041,258

(22) PCT Filed: Aug. 12, 2021

(86) PCT No.: PCT/EP2021/072518
§ 371 (c)(1),
(2) Date: Feb. 10, 2023

(87) PCT Pub. No.: WO2022/034178
PCT Pub. Date: Feb. 17, 2022

(65) Prior Publication Data
US 2023/0320964 A1    Oct. 12, 2023

Related U.S. Application Data

(60) Provisional application No. 63/064,564, filed on Aug. 12, 2020.

(51) Int. Cl.
*A61Q 5/10*    (2006.01)
*A61K 8/22*    (2006.01)
(Continued)

(52) U.S. Cl.
CPC .............. *A61K 8/4953* (2013.01); *A61K 8/22* (2013.01); *A61K 8/23* (2013.01); *A61K 8/42* (2013.01);
(Continued)

(58) Field of Classification Search
CPC .......... A61K 8/4953; A61K 8/22; A61K 8/23; A61K 8/42; A61K 8/4926; A61K 8/494;
(Continued)

(56) References Cited

U.S. PATENT DOCUMENTS

| | | | | |
|---|---|---|---|---|
| 3,341,539 A | * | 9/1967 | Max et al. | C09B 62/4409 8/549 |
| 4,428,750 A | * | 1/1984 | Birke | D06P 5/13 8/461 |
| 5,364,415 A | * | 11/1994 | Lewis | C09B 9/00 8/408 |

FOREIGN PATENT DOCUMENTS

| | | | | |
|---|---|---|---|---|
| GB | 852519 A | | 10/1960 | |
| GB | 999792 | * | 7/1961 | ............... C09B 9/02 |
| GB | 953172 A | | 3/1964 | |
| WO | WO 02096383 A1 | * | 12/2002 | ............. A61Q 5/065 |

OTHER PUBLICATIONS

STIC Search Report dated Jun. 8, 2024.*
(Continued)

*Primary Examiner* — Eisa B Elhilo
(74) *Attorney, Agent, or Firm* — Dennemeyer & Associates, LLC

(57) ABSTRACT

The disclosure relates to methods for coloring keratinous substrates using solubilized vat dyes, as well as compositions and kits suitable for carrying out the methods. The disclosure also relates to novel solubilized vat dyes.

24 Claims, 6 Drawing Sheets

(51) Int. Cl.
 A61K 8/23      (2006.01)
 A61K 8/42      (2006.01)
 A61K 8/49      (2006.01)
 C09B 9/02      (2006.01)
 C09B 67/22     (2006.01)
 C09B 67/44     (2006.01)
(52) U.S. Cl.
 CPC ............ *A61K 8/4926* (2013.01); *A61K 8/494* (2013.01); *A61Q 5/10* (2013.01); *C09B 9/02* (2013.01); *C09B 67/0034* (2013.01); *C09B 67/0083* (2013.01); *A61K 2800/884* (2013.01)
(58) Field of Classification Search
 CPC ............ A61K 2800/884; A61K 8/4946; A61K 8/4986; A61K 8/463; A61Q 5/10; C09B 9/02; C09B 67/0034; C09B 67/0083; C09B 67/0033; C09B 9/00
 USPC .................................................... 8/405, 461
 See application file for complete search history.

(56) References Cited

OTHER PUBLICATIONS

International Search Report received for PCT Patent Application No. PCT/EP2021/072518, mailed on Feb. 24, 2022.
Written Opinion of the International Searching Authority received for PCT Patent Application No. PCT/EP2021/072518, mailed on Feb. 24, 2022.

* cited by examiner left: sol vat yellow 4
right: Magma limoncello left: Vidal Sassoon yellow
right: sol vat yellow 4 left: sol vat yellow 4
right: Magma limoncello left: Vidal Sassoon yellow
right: sol vat yellow 4 left: sol vat yellow 4
right: Magma limoncello left: Vidal Sassoon yellow
right: sol vat yellow 4

METHOD AND COMPOSITION FOR COLORING A KERATINOUS SUBSTRATE USING SOLUBILIZED VAT DYES

CROSS-REFERENCE TO RELATED APPLICATIONS

This is a 35 U.S.C. 371 National Stage Patent Application of International Application No. PCT/EP2021/072518, filed Aug. 12, 2021, which claims priority to U.S. Provisional Application 63/064,564, filed Aug. 12, 2020, each of which is hereby incorporated by reference in its entirety.

BACKGROUND OF THE INVENTION

Treatments to mammalian or synthetic keratin fibers are known. Mammalian keratin fibers (natural hair) is structured as a cuticle or outer surface layer, a cortex which is an internal mid layer containing melanin or color bodies and keratin bundles, and a central core termed medulla. Typical dye treatments focus on changes of the cortex. Of particular note are cortex treatments that alter the appearance of the hair, for example by changing the color or reflective properties of hair. This can be achieved through treating hair cortex with a formulation containing dye molecules (so call direct dyes) which diffuse into or are absorbed through the cuticle of the hair fibers.

Alternatively, so-called oxidative dyes may be employed wherein the dye precursors (intermediates called primaries and couplers) diffuse into the cortex and then react to form colored species within the cortex of the hair. Often the oxidative dye products are designed to also lift the hair, decolorizing some of the melanin of the cortex to enable a wider range of colors to be achieved. Over time, the color imparted to the hair is removed during washing. This can happen rapidly for so called direct dyes, and leads to a short-term change in hair appearance, typically lasting for a few washes. The so-called oxidative dyes may last considerably longer, and indeed removing the color can be hard to achieve, even after a considerable number of washes. When oxidative dyes are eventually removed by washing out, the melanin has also been decolorized by bleaching so that it will not return to its original color but to a lighter color. Unfortunately, the process of decolorizing hair via bleaching technologies applied by intent leads not only to a lifting of the hair but also to a change in the perceived tone of the hair, resulting in what is often described as an off-tone or "brassy" result where the hair looks more orange than untreated hair of a similar lightness.

As an alternative hair coloring method, pigments may be adhered to the hair surface to alter the perceived color, however this approach normally only lasts until the hair is next washed.

One drawback of the known oxidation-based technologies in this area is that the lastingness of the coloration experience significantly slows down once more lifting (e.g. bleaching conditions) is applied. Even under gentle oxidative conditions at moderate alkaline pH (such as pH=9.0), the lastingness of various shades is not consistent, namely fashionable red tones always show greater tendencies to be washed out at a higher rate versus darker natural tones.

Another drawback of classic oxidative colorants is the inability to produce a wide range of brilliant shades across the entire spectrum which show a fully consistent long lastingness.

Another still unsolved problem is some significant "white zones" in the spectra which cannot be filled by standard oxidative hair colorants. For instance, fashionable orange shades cannot be accessed directly with oxidative coupling reagents and therefore, these color spaces need to be bridged with direct dyes which definitely show an inferior lastingness versus the oxidative coloration which leads to an inconsistent color experience until the customer refreshes the hair coloration by intent.

Another significant drawback of oxidative colorants becomes apparent when higher lifting standards are applied to completely discolor the natural melanin to obtain blond/bleached hair, and when simultaneously a new color is applied which is resistant towards more harsh oxidative conditions. Such a procedure is absolutely not achievable with oxidative colorants using primaries and couplers of any origin. Today, selected direct dyes, mainly anionic dyes, have proven to be resistant to bleaching conditions as described by Said et. al. (U.S. Pat. No. 7,189,265B2). Even this was correctly regarded being a breakthrough discovery, the main disadvantages related to lastingness remain unsolved. The unsolved lastingness is especially a disadvantage, for instance, when blue dyes described in U.S. Pat. No. 7,189,265B2 (e.g. tetrabromophenol blue), which are resistant to bleaching conditions, are also used to consolidate the brassy blond tone after bleaching of virgin hair to achieve an appealing cosmetic result as attractive blond shades. However, the blue direct dye is fading quickly after 1-3 washes and the brassy blond effect is back again.

A drawback of alternative coloring concepts using pigments is the low adherent fastness of the pigment or colored material to the keratin fibers.

There is therefore a need for hair coloring compositions and methods that address the foregoing drawbacks of known technologies. The present invention addresses this need by providing methods, compositions and kits for coloring keratinous substrates, which avoid the drawbacks of oxidative hair coloring technology, provide for long lasting coloring, and enable a wide range of colors including shades and hues that cannot be accessed by oxidative hair coloring technology. In addition, the methods of the present invention allow for simultaneous lifting of hair, over the complete spectrum covering mild oxidative lifting to harsh bleaching conditions.

The concept of using solubilized vat dyes according to the present invention, in particular from the broader family of Indanthren dyes (e.g. featuring anthrachinones, acridine, perylene, naphthaline and violanthrone backbones) presents a unique, novel and versatile stand-alone oxidative hair coloring technology enabling the full professional color palette of shades without using any of conventional oxidative components such as primaries and couplers. Hair colorations using these solubilized vat dyes show an ultra-permanent lastingness with extraordinary wash and lightfastness properties throughout any oxidative stage which are commonly known, starting from mild oxidative conditions at hydrogen peroxide levels <2.0% up to bleaching conditions using hydrogen peroxide levels at 12.0%, even in combination with persulfate salts. This concept provides for the first time ever the full flexibility and artistic freedom creating any possible shade (natural and highly brightening fashion shades) with unlimited freedom grades on oxidation/lifting levels using the same set of dye compounds.

U.S. Pat. No. 5,364,415A (Lewis et al.) discloses a hair coloring method based on a mild oxidative hair coloring system comprising primary intermediates and couplers, which method contemplates additionally applying one of seven selected solubilized vat dyes to the hair, as color brightening special ingredients, in order to obtain brighter red and yellow colors than obtainable with the common oxidative colorants alone.

DE102004014764A1 (Javet et al.) discloses a hair coloring agent comprising a vat dye and a reducing agent forming an enediol under alkaline conditions, which reducing agent converts the vat dye to the leuco form under alkaline conditions. The reference discloses stabilizing the leuco form by appropriate packaging, a protective gas blanket, the addition of stabilizing and/or protecting substances (for example cationic compounds such as polymers, tensides, metal ions), or esterification. DE102004014763A1 (Javet et al.) discloses a similar hair coloring agent wherein the vat dye is an indigoid vat dye, the composition again comprising the reducing agent forming an enediol under alkaline conditions, further comprising a cationic compound.

US2003/0074745A1 (Vainshalboim et al.) discloses a method and system for dyeing hair without using a chemical oxidant. The dyes used are solubilized indigoid and anthraquinone vat dyes.

US2011/0189116A1 (Gauche et al.) discloses a method of coloring a material, comprising applying to the material a composition comprising a sulfur-containing nucleophile; and applying to the material a composition comprising a dye compound other than a reactive dye.

SUMMARY OF THE INVENTION

This invention discloses a novel and highly versatile oxidative hair coloring system which addresses most of current concerns related to oxidative hair colorings. Moreover, we describe a dedicated set of solubilized vat dyes which are easily to apply to hair for professional users such as hair stylists which show absolute comparable properties in terms of light and wash fastness which is unique and a new experience among the status quo of commercially available oxidative dyes. These dyes are commonly and commercially used also for dyeing sensitive fabrics such as silk. The invention uses leuco vat dye sulfuric esters, which are obtained from the vat dye pigments via reduction in alkaline medium to give the leuco form, followed by treatment with chloro-sulfonic acid or simply sulfur-trioxide. Leuco vat dye sulfuric esters and methods for producing same are disclosed for example in DE1117242B. The leuco vat dye sulfuric esters can be rapidly cleaved to form the classic leuco form of the corresponding vat dye. Subsequent oxidation precipitates the insoluble vat dye as pigment. The terms "solubilized vat dye", "leuco vat dye sulfuric ester" and "sulfuric ester of a vat dye" are used interchangeably in the present disclosure.

According to a first aspect, the present invention provides a method for coloring a keratinous substrate. The method comprises applying a first composition (also denoted herein as composition A) to the keratinous substrate, which composition comprises an aqueous medium and a solubilized vat dye dissolved in the medium. The solubilized vat dye is a leuco vat dye sulfuric ester. This first composition is essentially free of oxidative dye precursors selected from primary intermediates and couplers. According to an embodiment, the first composition is free of oxidative dye precursors selected from primary intermediates and couplers. The method further comprises applying a second composition (also denoted herein as composition B) to the keratinous substrate. This second composition has a pH in the range of 3.0-5.0. The method optionally further comprises applying a third composition (also denoted herein as composition C) to the keratinous substrate, which composition comprises an oxidizing agent.

According to a second aspect, the present invention provides a method for correcting a brassy color shade or hue of hair. The method is particularly suitable for correcting a brassy color shade or hue of lifted mammalian hair such as human scalp. The method comprises applying a first composition (also denoted herein as composition AA) to the hair, which composition comprises an aqueous medium and a solubilized vat dye dissolved in the medium. The solubilized vat dye is a leuco vat dye sulfuric ester. The leuco vat dye sulfuric ester(s) present in the first composition are derived from vat dyes giving overall a blue or bluish color. This first composition is essentially free of oxidative dye precursors selected from primary intermediates and couplers. According to an embodiment, the first composition is free of oxidative dye precursors selected from primary intermediates and couplers. The method further comprises applying a second composition (also denoted herein as composition BB) to the hair. This second composition has a pH in the range of 3.0-5.0. The method optionally further comprises applying a third composition (also denoted herein as composition CC) to the hair, which composition comprises an oxidizing agent.

According to a third aspect, the present invention provides a method for changing the color of a vat-dye-colored keratinous substrate. The method is suitable for changing the color of a keratinous substrate which previously had been colored by the method according to the present invention for coloring a keratinous substrate. The said method is also suitable for changing the color of mammalian hair the color shade or hue of which previously had been corrected by the method according to the present invention for correcting a brassy color shade or hue of lifted mammalian hair. The correction method comprises applying to the keratinous substrate a fourth composition (also denoted herein as composition D) having a pH in the range of 11.0-12.0. Composition D further comprises a reducing agent.

According to a fourth aspect, the present invention provides a composition for coloring a keratinous substrate. The composition corresponds to first composition (composition A or AA) of the methods of the present invention. The composition comprises an aqueous medium and a solubilized vat dye dissolved in the medium, which solubilized vat dye is a leuco vat dye sulfuric ester. The composition is essentially free of oxidative dye precursors selected from primary intermediates and couplers. According to an embodiment, the composition is free of oxidative dye precursors selected from primary intermediates and couplers.

According to a fifth aspect, the present invention provides a kit for coloring a keratinous substrate. The kit comprises a first compartment (also denoted herein as compartment A) comprising a leuco vat dye sulfuric ester or salt thereof. The kit further comprises a second compartment (also denoted herein as compartment B) comprising an acid or salt thereof. According to embodiments, the kit may further comprise one or more additional compartments comprising components useful in the methods according to the present invention.

According to a sixth aspect, the present invention provides novel leuco vat dye sulfuric esters, or salts thereof. In particular, the present invention provides the following leuco vat dye sulfuric esters or salts thereof:
  solubilized Pigment Violet 19 according to formula (I),
  solubilized Pigment Red 122 according to formula (II),
  solubilized Pigment Red 194 according to formula (III), solubilized Pigment Orange 43 according to formula (IV),
solubilized tetraazaviolanthron-trans-black according to formula (V),
solubilized tetraazaviolanthron-cis-black according to formula (VI),
solubilized perylene-amidine-trans-blue according to formula (VII),
solubilized perylene-amidine-cis-blue according to formula (VIII),
solubilized naphthaline-amidine-trans-blue according to formula (IX), and
solubilized naphthaline-amidine-cis-blue according to formula (X).

Formulae (I) through (X) are depicted in the detailed description.

According to a seventh aspect, the present invention provides for the use of the above leuco vat dye sulfuric esters in vat dyeing processes, in particular for coloring keratinous substrates.

According to an eighth aspect, the present invention provides substrates, in particular fibrous substrates having adsorbed thereto a novel leuco vat dye sulfuric ester according to the present invention.

The vat dyes used according to the teachings of the present invention are not susceptible to oxidative degradation, and therefore can be applied over all oxidation levels without any restriction to the user. Hence, for the first time, a holistic and universal solution in the oxidative dyeing area can be introduced without making any compromise as these vat dyes can be applied under mild oxidative conditions with very moderate to low lift of virgin hair and as well equally under more harsh conditions such as bleaching with no loss in lastingness. The coloring process will not take longer than 1 h in average which is comparable to most of the standard oxidative hair colorations. It comprises 1) a penetration phase into swollen hair via mild alkaline conditions (ca. pH=9.0), 2) a short reactive phase which is started while decreasing the pH value to gentle acid conditions (ca. pH=3.5) where the sulfuric ester group is hydrolyzed, followed by 3) controlled precipitation (oxidation) of the corresponding vat dye as insoluble vat pigment inside the cortex under alkaline conditions (pH range 9.0-11.0) via air oxygen, peroxide or bleaching agents such as persulfate salts.

BRIEF DESCRIPTION OF DRAWINGS

FIG. 1 shows a switch of natural blonde human hair treated with solubilized vat violet 1 C.I.60011, CAS 1324-57-8 (100 mg in 10 mL solvent; 1% by weight); oxidation conditions including 9% hydrogen peroxide, pH=9.0

FIG. 2 shows a switch of natural blonde human hair treated with solubilized vat yellow 4 C.I.59101, CAS 3564-70-3 (100 mg in 10 mL solvent; 1% by weight); oxidation conditions including 12% hydrogen peroxide, Blondor powder=bleaching powder, comprising peroxodisulfates, commercial brand of the Wella Company.

FIG. 3 shows a switch of natural blonde human hair treated with solubilized vat yellow 4 C.I.59101, CAS 3564-70-3 (100 mg in 10 mL solvent; 1% by weight); oxidation conditions including 9% hydrogen peroxide, pH=9.0

FIG. 4 shows a switch of natural dark brown (5/0) human hair treated with solubilized vat green 1 C.I.59826, CAS 2538-84-3 (100 mg in 10 mL solvent; 1% by weight); oxidation conditions including 12% hydrogen peroxide, Blondor powder=bleaching powder, comprising peroxodisulfates, commercial brand of the Wella Company.

FIG. 5 shows a switch of natural dark brown (5/0) human hair treated with solubilized vat violet 1 & solubilized vat green 4 (1:1), (50 mg each in 10 mL solvent; 1% by weight dye content); oxidation conditions including 12% hydrogen peroxide, Blondor powder=bleaching powder, comprising peroxodisulfates, commercial brand of the Wella Company.

FIG. 6 BELOW shows a switch of natural dark brown (5/0) human hair treated with oxidation conditions including 12% hydrogen peroxide, Blondor powder=bleaching powder, comprising peroxodisulfates, commercial brand of the Wella Company. (no dye addition as reference showing the brassy blond effect)

FIG. 7 ABOVE shows a switch directly after coloration ("fresh ON"), while FIG. 7 BELOW shows color remanence of an identically colored switch after 15 washes with shampoo.

FIG. 8 ABOVE shows a switch directly after coloration ("fresh ON"), while FIG. 8 BELOW shows color remanence of an identically colored switch after 15 washes with shampoo.

DEFINITIONS

Figure 1:
FIGS. 1-5 show hair switches colored according to the present disclosure via application of the indicated solubilized vat dye(s), hydrolysis of the ester(s), and oxidation under the indicated conditions.
Figure 2:
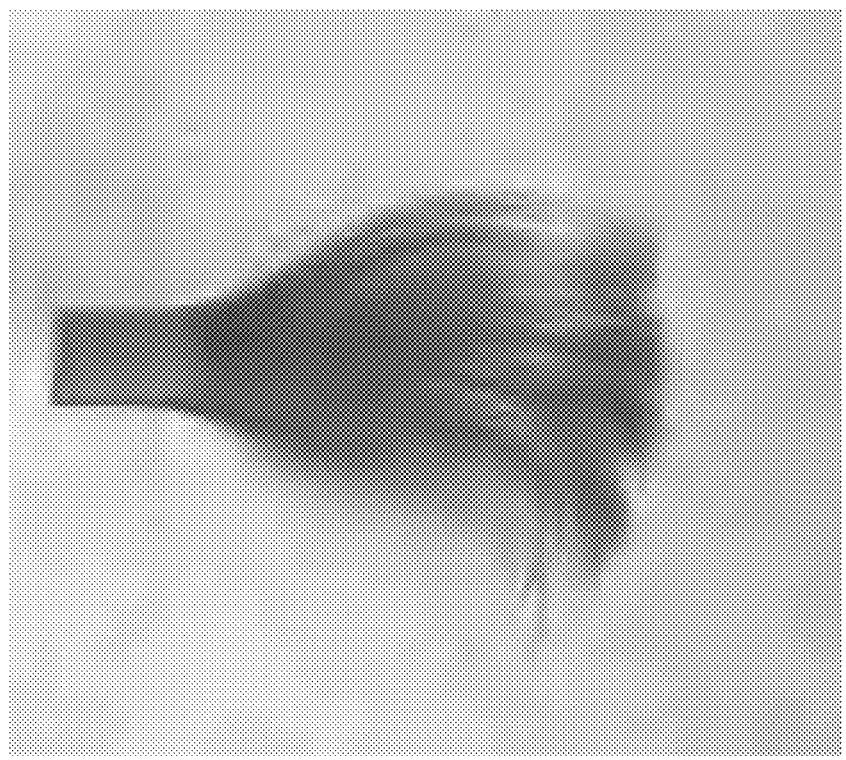
Figure 3:
Figure 4:
Figure 5:
Figure 6:
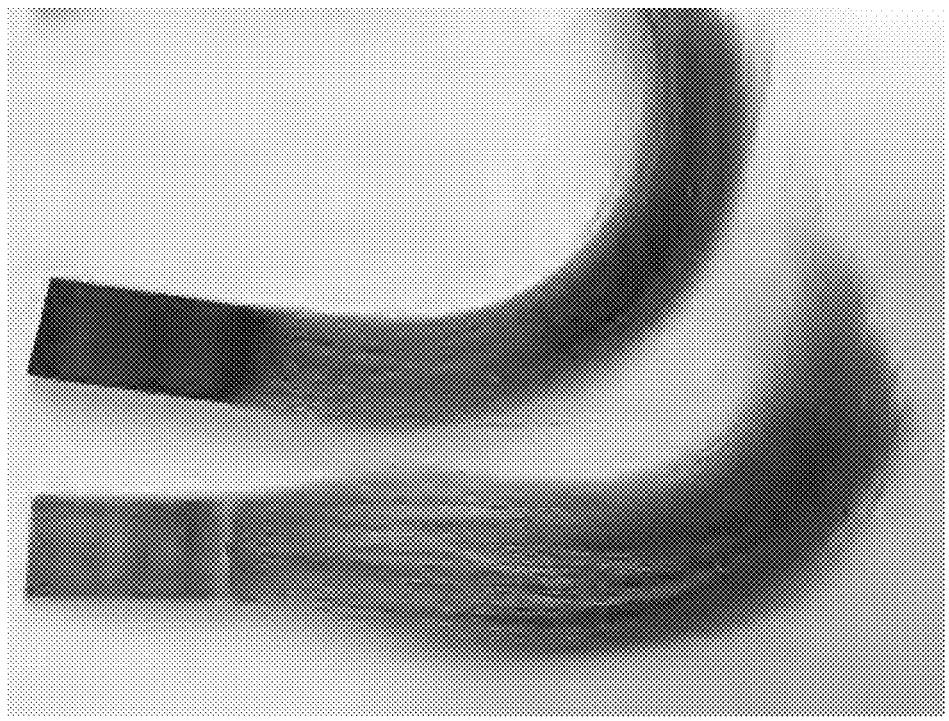
FIG. 6 ABOVE shows a switch of natural dark brown (5/0) human hair treated with solubilized vat blue 4 (10 mg in 10 mL solvent; 0.1% by weight dye content); oxidation conditions including 12% hydrogen peroxide, Blondor powder=bleaching powder, comprising peroxodisulfates, commercial brand of the Wella Company.
Figure 7:
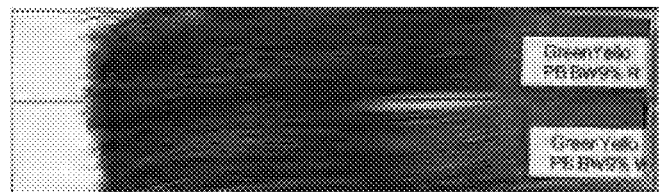
FIG. 7 shows switches of natural blonde human hair treated with solubilized vat green 1 & solubilized vat yellow 4 (2:1); oxidation conditions including 9% hydrogen peroxide, Blondor powder=bleaching powder, comprising peroxodisulfates, commercial brand of the Wella Company.
Figure 8:
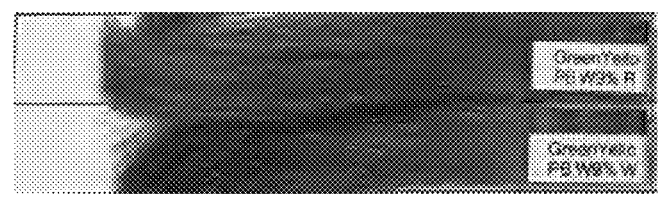
FIG. 8 shows switches of natural blonde human hair treated with solubilized vat green 1 & solubilized vat yellow 4 (1:1); oxidation conditions including 9% hydrogen peroxide.
Figure 9:
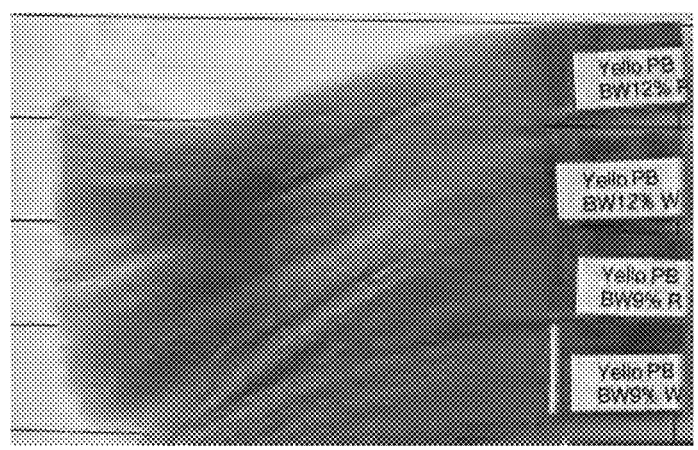
FIG. 9 shows two pairs of switches of natural blonde human hair treated with solubilized vat yellow 4 (1:1); oxidation conditions including 9% or 12%, respectively, hydrogen peroxide, Blondor powder=bleaching powder, comprising peroxodisulfates, commercial brand of the Wella Company. The upper pair shows coloration after oxidation with 12% hydrogen peroxide, the upper switch as obtained directly after coloration ("fresh ON"), and the lower switch after 15 washes with shampoo. The lower pair shows coloration after oxidation with 9% hydrogen peroxide, again the upper switch as obtained "fresh ON", and the lower switch after 15 washes with shampoo.
Figure 10:
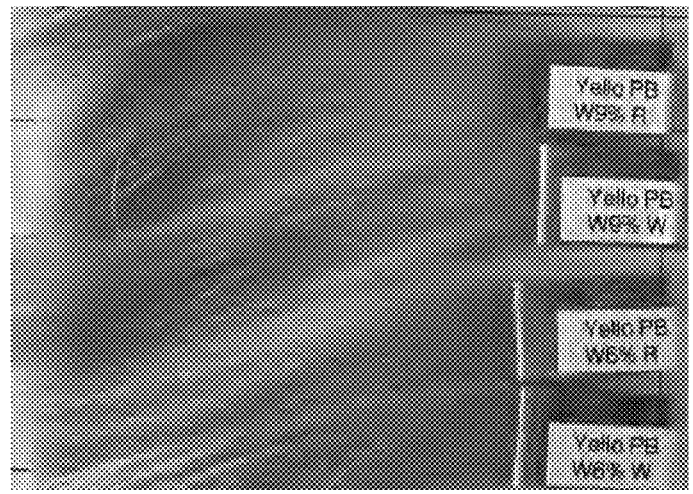
FIG. 10 shows two pairs of switches of natural blonde human hair treated with solubilized vat yellow 4; oxidation conditions including 9% or 6%, respectively, hydrogen peroxide. The upper pair shows coloration after oxidation with 9% hydrogen peroxide, the upper switch as obtained "fresh ON", and the lower switch after 15 washes with shampoo. The lower pair shows coloration after oxidation with 6% hydrogen peroxide, again the upper switch as obtained "fresh ON", and the lower switch after 15 washes with shampoo.

As used in the specification and the appended claims, the singular forms "a," "an" and "the" include plural referents unless the context clearly dictates otherwise.

The term "may" in the context of this application means "is permitted to" or "is able to" and is a synonym for the term "can." The term "may" as used herein does not mean possibility or chance.

The term "and/or" in the context of this application means one or the other or both. For example, an aqueous solution of A and/or B means an aqueous solution of A alone, an aqueous solution of B alone and an aqueous solution of a combination of A and B.

The term "about" is understood to mean±10 percent of the recited number, numbers or range of numbers. According to embodiments, the term "about" is understood to mean±2 percent of the recited number, numbers or range of numbers.

The term "about 0% by weight" is understood to mean that no substance, compound or material to which zero (0) refers is present, up to a negligible but detectable amount is present, assuming that detectability is on a ppm (parts per million) basis.

Where features or aspects of the invention are described in terms of Markush groups, those skilled in the art will recognize that the invention is also thereby described in terms of any individual member or subgroup of members of the Markush group. For example, if X is described as selected from the group consisting of methyl, ethyl or propyl, claims for X being methyl and claims for X being methyl and ethyl are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4. Similarly, values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range.

The term "keratinous substrates" as used herein means any natural or synthetic substrate made of or comprising a keratin. In particular, the term "keratinous substrates" encompasses natural and synthetic keratin fibers. Preferred keratinous substrates are natural keratin fibers. Natural keratin fibers include those from mammals and/or on mammals including human, primate, ruminant, camelid, equine, rodent and neovison including but not limited to cow, sheep, deer, goat, buffalo, lama, alpaca, camel, guanaco, vicuna, horse, antelope, moose, elk, rat, mouse, beaver, rabbit, mink, monkey, ape and similar species. Natural keratin fibers may include hair, fur or nails. Particularly preferred keratinous substrates in the present disclosure are mammalian keratin fibers, in particular human scalp. The term "keratin fibers" is used interchangeably in this document with the terms "hair" or "hair strands" unless the context dictates otherwise.

As used herein, the term "optionally" means that the corresponding substituent or thing may or may not be present. It includes both possibilities.

The term "water-soluble" as used herein refers to a solubility at 25° C. in the aqueous medium of the composition for treating keratinous substrates of at least 1.0% by weight, in particular at least 5.0% by weight, for example at least 10.0% by weight such as at least 25.0% by weight.

The term "composition" as used herein denotes a mixture or blend comprising at least two components. Typical compositions comprise at least one functional component (such as, for example, a leuco vat dye sulfuric ester, or a pH adjuster, or an oxidizing or reducing agent) and at least one solvent component (such as water or an alcohol). A composition may be present in any suitable physical form, including for example liquids of varying viscosities, gels, foams, creams, and the like. The term "composition" typically denotes the ready-to-use composition unless the context dictates otherwise. "Ready-to-use" denotes the form in which the composition is actually applied to a keratinous substrate such as mammalian hair, in particular human scalp.

The term "alkalizer" as used herein denotes any compound suitable for adjusting the pH of a composition in the alkaline range. Typical alkalizers comprise bases such as NaOH, ammonia, urea, pyridine, aminomethylpropanol (AMP), monoethanolamine, DBU (diazabicyclo-undecane). Pyridine and DBU may give create safety issues and for that reason are less preferred.

The term "essentially free" of a particular component denotes an amount of less than 1.0% by weight of the respective component in an entity such as a composition, based on the total weight of the entity. In particular, the term "essentially free" denotes an amount of less than 0.5% by weight, for example less than 0.1% by weight, such as 0.01% by weight of the respective component in the entity. The term "free" of a particular component denotes an amount below the detection limit, assuming that detectability is on a ppm (parts per million) basis.

DETAILED DESCRIPTION

1 The Solubilized Vat Dyes

Vat dyes are known and have been used for many decades as powerful dyes and pigments for textile dyeing. Especially those of the Indanthren family show superior properties regarding light fastness, wash fastness, are stable to any oxidizing events and are extremely weather proof. In addition, they do show remarkable melting points >100° C.

which indicates the high chemical stability. The only option for chemically modifying them is applying reductive processes in order to convert them to a soluble and therefore processable form. The soluble form of the vat dyes is also known as the "leuco" form. The typical scheme of transformation options is as depicted in scheme 1.

Scheme 1

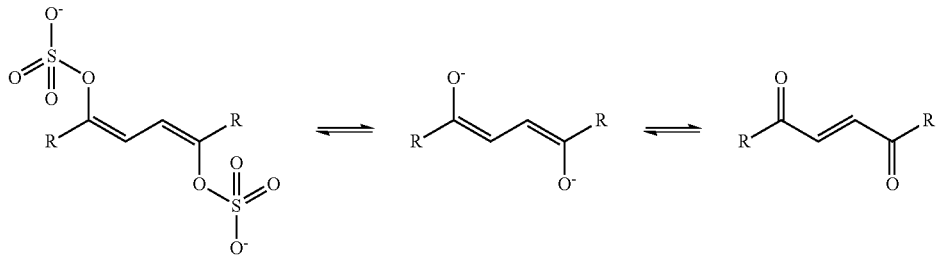

Harsh alkaline conditions are typically required in order to reduce vat dyes (formula at the right in scheme 1) to their corresponding leuco form (middle formula in scheme 1), in which soluble leuco form they are able to be applied in solution and penetrate into keratinous fibers as soluble dyes. It is not possible, however, to apply such harsh conditions (pH>13.0) to delicate (sensitive) keratinous fibers or living objects. The sulfuric esters of the vat dye leuco form (formula to the left in scheme 1) represent a reactive and readily soluble form of vat dye pigments. They can be used under significantly milder conditions, and therefore are suitable for coloring sensitive substrates (e.g. natural fibers) or substrates present on living objects, thus bypassing the harsh conditions needed for the leuco form vat dyes.

The leuco vat dyes sulfuric esters are perfect candidates as this structural element opens the space to many chromophores which can be modified as such. The ideal chromophore candidate needs to have at least 2 carbonyl groups where reduction and oxidation steps can be applied according to the scheme above, in combination with an extended aromatic electronic π-system. These solubilized sulfuric ester vat dyes show a totally unexpected ability to penetrate deeply into the cortex of the hair under mild alkaline conditions (pH=9.0), optionally in presence of swelling promotors such as urea or ammonia. This observation is not obvious given the size and bulky structure of the chromophores.

Other, also bulky dyes such as for instance direct dyes (e.g. azo dyes, antrachinone dyes etc.) with anionic or cationic charges, known in the literature, are observed to exhibit an only very moderate to even low penetration into the hair cortex. Consequently, these traditional direct dyes are merely adsorbed on the outer surface of hair, which can be shown via microscopic observation of cross sections of hair. Hence, the penetration property of the solubilized vat dyes is remarkable and results in an outstanding lastingness of the color achieved as compared to other chromophores such as the direct dyes mentioned above.

After the penetration phase under alkaline conditions is completed, hydrolysis of the labile sulfuric ester group is forced by reducing the pH value to moderately gently acid conditions pH=3.5) to obtain the pure reduced leuco form which is then rapidly oxidized in presence of air oxygen, hydrogen peroxide and/or bleaching ingredients such as persulfate salts. Once the vat dye pigments are precipitated in the cortex of the hair after the re-oxidation is completed, an exceptional ultra-long-lasting hair coloration is achieved. This is caused by an extremely low solubility of the formed pigments in aqueous environments. Hence, this type of coloration provides extremely long-lasting colorations which show extraordinary wash fastness. After >15 washes with shampoo, the so-treated hair remains completely unchanged while the entire color load is still there, with no traces of any loss.

However, hair coloring has reached high attention of toxicologists and is subject to safety clearance by authorities before the compounds can be used in commercial hair color formulations. Hence, appropriate chromophore structures should be selected to provide vat dyes which can be turned into commercial applications. Unlike the prior art in U.S. Pat. No. 5,364,415 (Lewis et. al.), where no selection of commercially available solubilized vat dyes has been made, it is the intention of the present disclosure to propose a variety of dedicated vat dyes which have a high likelihood to meet all criteria of toxicological pre-requisites. The most important question is if these dyes have the ability to penetrate through skin. Most of all previously published dyes used for hair coloring, regardless if applied under non-oxidative or oxidative conditions, do show a significant tendency to penetrate the skin, simply caused by their water solubility as hydrophilic, anionic or cationic dyes which is a mandatory requirement to process them onto hair fibers. Hence, sophisticated and cost intense toxicological evaluations are required in order to obtain safety clearance by authorities. An important improvement versus the state of the art would be excluding principally any skin penetration. It is common sense that pigments such as the finally precipitated vat dyes are completely insoluble and not bio-available and therefore not of interest for further toxicological evaluations. Hence, the focus here obviously is on the solubilized vat dyes as the intermediate form, which is applied on the hair fiber to allow penetration into the cortex of the hair. Hence, according to the present invention, chromophores with large and extended electronic π-systems are preferably contemplated to obtain an acceptable safety evaluation. That excludes all indigoid vat dyes as their molecular weight is regarded to be too low and they will likely penetrate easily through skin. On the other hand, the previously mentioned vat dyes and solubilized vat dyes, respectively, exhibit high molecular weight and the chromophore design is characterized by an even and extended bulky, aromatic polycyclic hydrocarbon surface. This bulky structure shows great hydrophobicity and steric hinderance which significantly decreases the probability of skin penetration. This is emphasized by the relatively moderate Log P values (see a selection of solubilized vat dye Log P values in scheme 2) of the solubilized vat dyes which show a remarkable low hydrophilicity provided their extraordinarily good solubility in water caused by the minimum of 2 sulfuric ester groups (see Log WS values).

Scheme 2:

| vat dye sulfuric ester | LogP | LogWS (intrinsic water solubility) |
| --- | --- | --- |
| solubilized vat blue 6 | −0.21 | −2.41 |
| solubilized vat orange 3 | 3.08 | −1.83 |
| solubilized vat orange 9 | 3.64 | −3.36 |
| solubilized vat red 10 | −0.33 | −1.81 |
| solubilized vat red 34 | −1.56 | −1.94 |
| solubilized vat yellow 1 | 2.65 | −2.48 |
| solubilized vat yellow 4 | 2.83 | −1.41 |
| solubilized vat violet 1 | 5.15 | −3.19 |
| solubilized vat blue 4 | −1.2 | −1.64 |
| solubilized vat green 1 | 2.89 | −3.97 |

Another issue in regard to the toxicological evaluation of the solubilized vat dyes in comparison to other widely used oxidative hair color intermediates is the fact that the selection of solubilized vat dyes do not have any aromatic amine function without any exception. Most of the traditional oxidative hair colorants are aromatic amines and therefore of high concern for consumer health. Net, the combination of not showing any aromatic amine function and the expected low ability to penetrate skin due to the chromophore design are clear advantages versus oxidative colorants known from the state of the art.

Having said that the obtained hair colorations are ultra-long lasting which is a great and unique observation, a professional hair product needs to show the ability to be adjusted in case something went wrong during the coloring service or the customer may not be satisfied with a certain color result. Traditional oxidative hair colorants using primaries and couplers to create the colored molecules can be adjusted or corrected if needed within certain boundaries. This is done via bleaching operations to crack the chromophore as standard oxidation hair colors are not stable to bleaching conditions. Obviously, this concept would not work for the vat dyes as they show, as already mentioned, a remarkable stability versus oxidative operations which are common to be performed on human hair. The only option here is to convert the vat dye pigments again back into their leuco forms via reductive conditions. In a first step the hair needs to swell under moderate alkaline conditions using urea or ammonia, so the hair fibers may then release the leuco forms. In a second step, a reducing agent such as sodium dithionite or hydroxy-acetone is applied excessively at 25-50° C., for example 35-40° C. for about 1 h. After the hair is rinsed and shampooed, a moderate loss of color and brilliance is observed which is sufficient to adjust a color shade or correct a certain color observation.

The dyes are typically selected from the overall dye family "Indanthren" dyes which is more a synonym for extra stable dyes with excellent fastness properties rather referring to a dedicated chemical class. Even though, most of the suitable chromophores according to the present disclosure are selected from dyes based on naphthalene, perylene, antrachinone and violanthrone backbones. As already mentioned, all do have in common that they have no aromatic amine function but have at least 2 carbonyl groups to be modified to the solubilized sulfuric ester intermediate which is regarded to be the reactive color ingredient for this oxidative hair dyeing system.

These commercial dyes are manufactured according to ta standard procedure from commercial vat dye pigments (see DE1117242). The reduction is carried out in alkaline medium using n-methyl acetamide, potassium boranate, sodium dithionite, followed by sulfatization in the presence of sulfur trioxide and di-chloro ethane as solvent. Alternatively, the reaction can be carried out in pyridine as alkalizer and using chlor-sulfonic acid to yield the sulfuric ester. This is exemplary shown for solubilized vat green 1 in scheme 3:

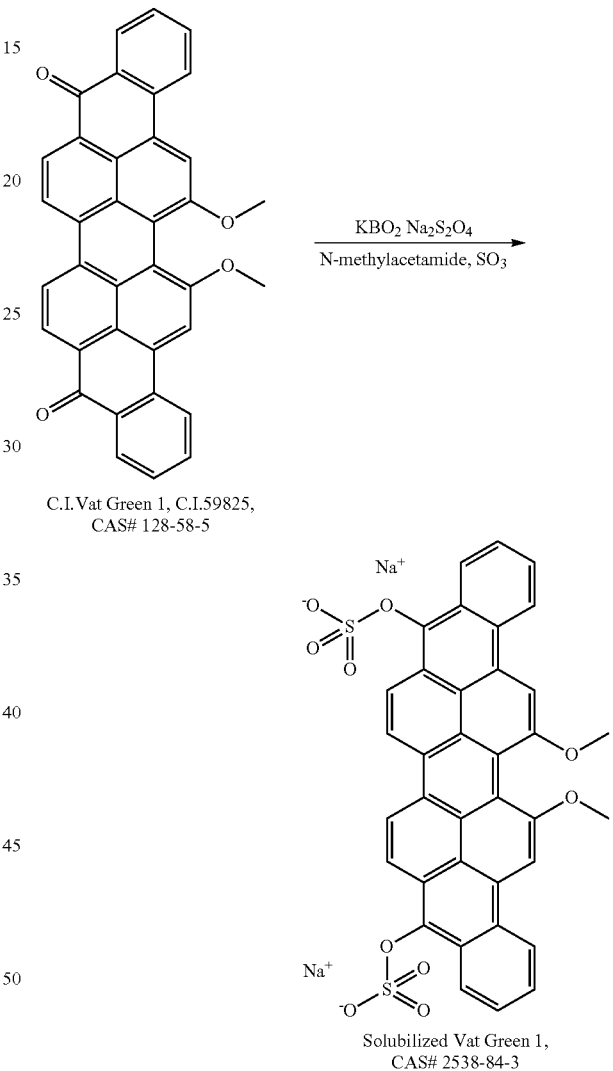

Examples of preferred solubilized vat dyes are solubilized vat blue 4 (CAS #747-19-5), solubilized vat violet 1 (CAS #1324-57-8), solubilized vat yellow 4 (CAS #3564-70-3), solubilized vat green 1 (CAS #2538-84-3), solubilized vat yellow 1 (CAS #6487-09-8), solubilize vat red 34 (CAS #12226-70-9), solubilized vat red 10 (CAS #10126-90-6), solubilized vat orange 9 (CAS #70356-06-8), solubilized vat orange 3 (CAS #10290-03-6), solubilized vat blue 6 (CAS #2519-28-0), solubilized vat yellow 7 (CAS #3956-62-5), solubilized vat brown 1 (CAS #23725-15-7) and solubilized vat blue 20 according to the following structures in scheme 4:

Scheme 4
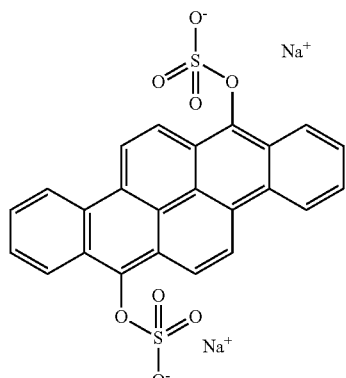
Solubilized Vat Yellow 4,
CAS# 3564-70-3
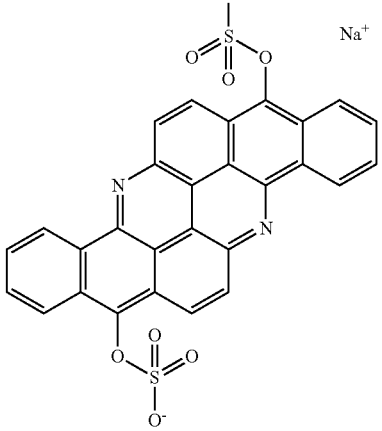
Solubilized Vat Yellow 1, CAS# 6487-09-8
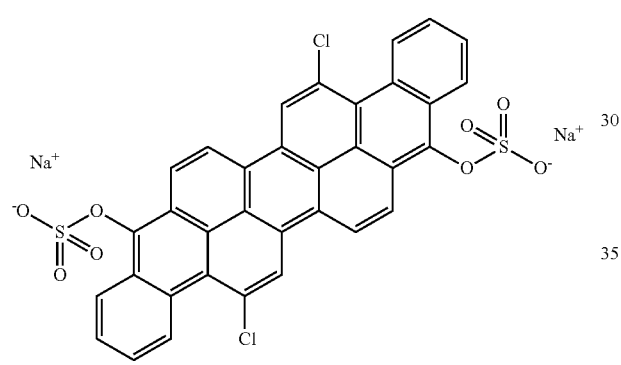
Solubilized Vat Violet, 1 CAS# 1324-57-8
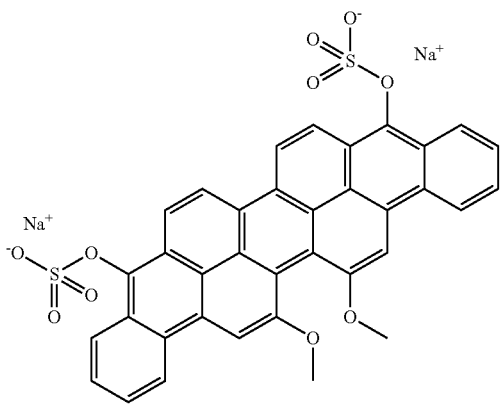
Solubilized Vat Green 1, CAS# 2538-84-3
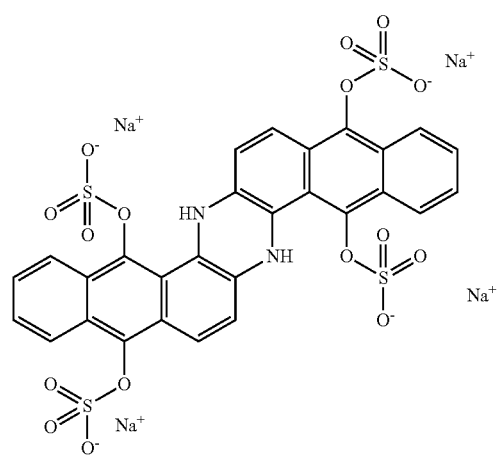
Solubilized Vat Blue 4, CAS# 2747-19-5
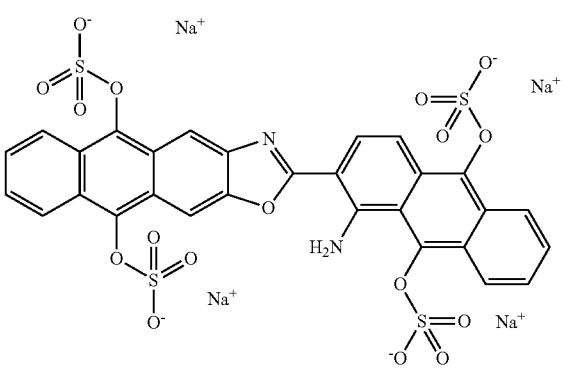
Solubilized Vat Red 10, CAS# 10126-90-6

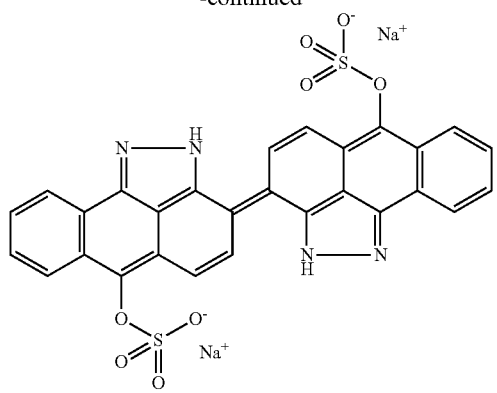
Solubilized Vat Red 34, CAS# 12226-70-9
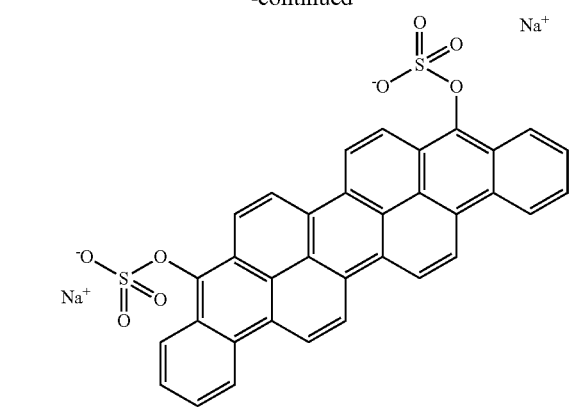
Solubilized Vat Blue 20
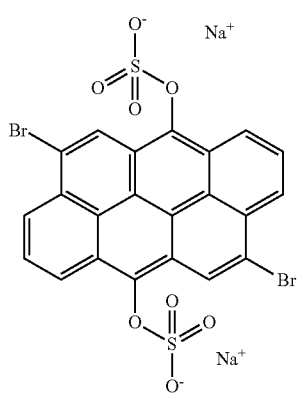
Solubilized Vat Orange 3, CAS# 10290-03-6
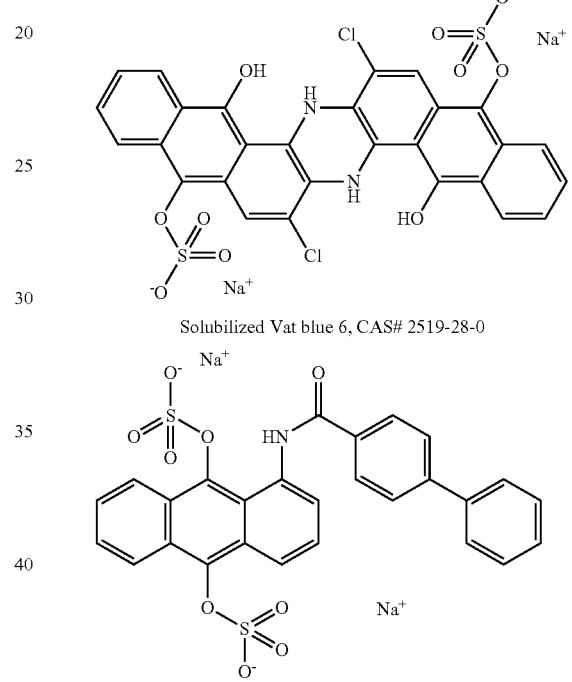
Solubilized Vat blue 6, CAS# 2519-28-0
Solubilized Vat Yellow 7, CAS# 3956-62-5
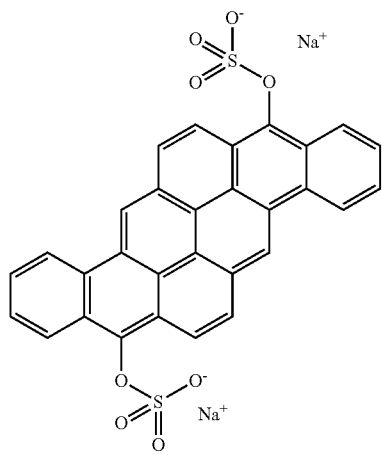
Solubilized Vat Orange 9, CAS# 70356-06-8
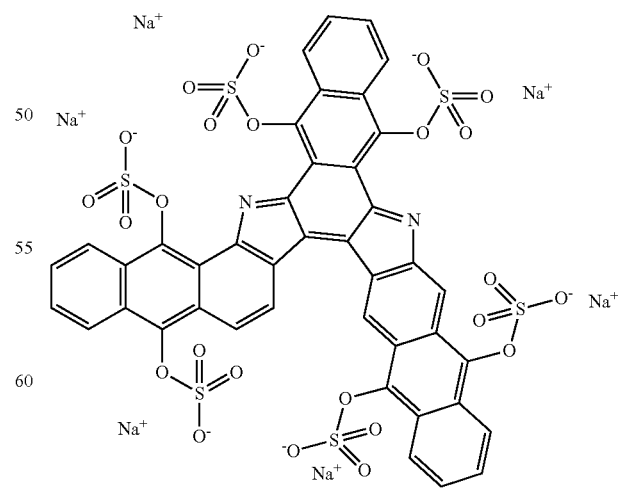
Solubilized Vat brown 1 (CAS# 23725-15-7)

1.1 Novel Solubilized Vat Dyes

According to an aspect, the present invention provides novel solubilized vat dyes. Based on the above synthesis concept, further non-commercial solubilized vat dyes, not previously known in the literature, may be obtained. It has surprisingly been found that not only classic vat dyes showing at least 2 carbonyl groups and an aromatic polycyclic hydrocarbon surface are useful starting materials, but also known orange, red, blue and black pigments derived from naphthaline and perylene bis-amidines can be converted into the related sulfuric ester derivatives. Shown below in scheme 5, the conversion for the 2 isomers of Indanthren scarlet (Pigment orange 43, trans-form and Pigment Red 194, cis-form) to yield the corresponding sulfuric ester (see DE1117242) is shown. The conversion is carried out under standard alkaline and reductive conditions followed by sulfatization using sulfur trioxide.

Novel solubilized vat dyes may as well be obtained starting from the commercially available vat dyes shown below in scheme 6:

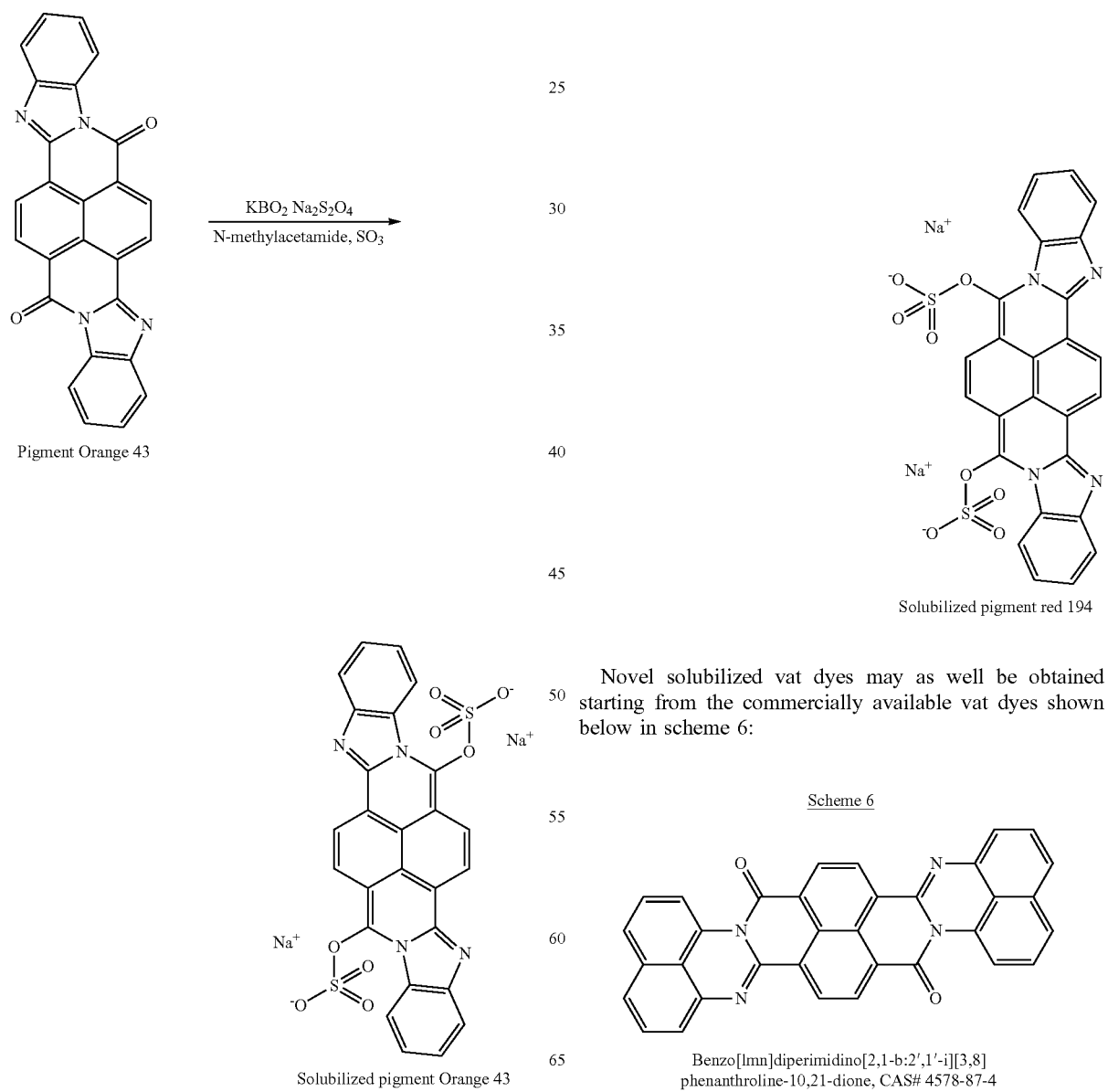

Benzo[lmn]diperimidino[2,1-b:2′,1′-i][3,8]
phenanthroline-10,21-dione, CAS# 4578-87-4

-continued

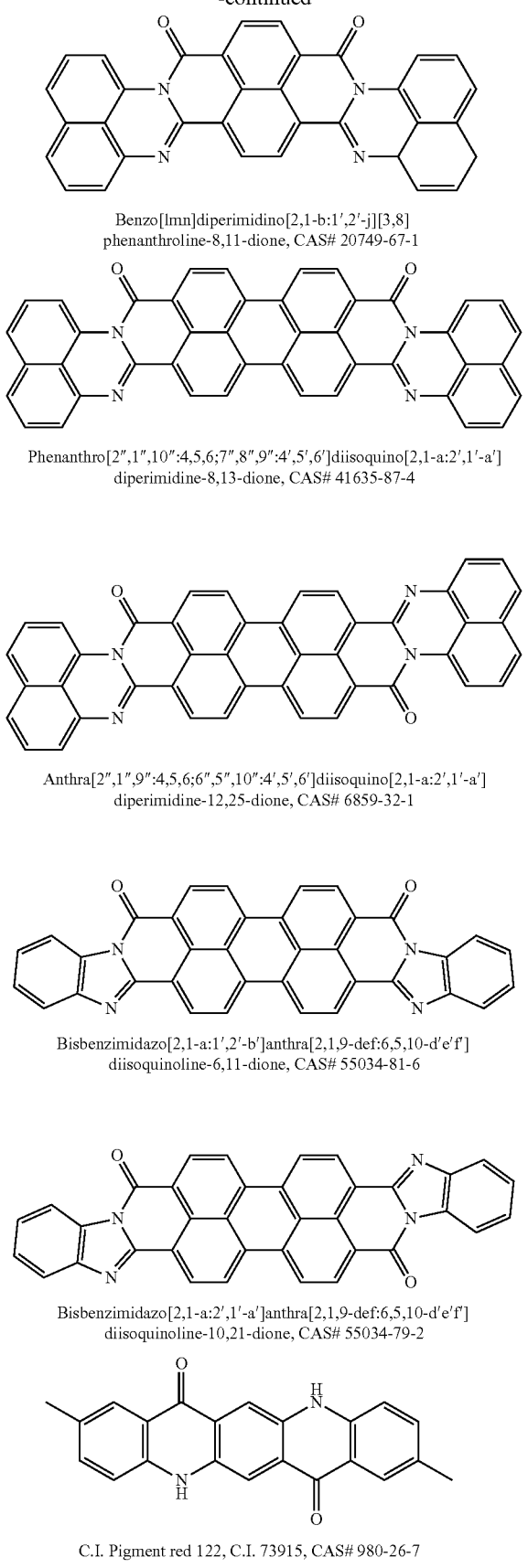

Benzo[lmn]diperimidino[2,1-b:1',2'-j][3,8]
phenanthroline-8,11-dione, CAS# 20749-67-1

Phenanthro[2″,1″,10″:4,5,6;7″,8″,9″:4',5',6']diisoquino[2,1-a:2',1'-a']
diperimidine-8,13-dione, CAS# 41635-87-4

Anthra[2″,1″,9″:4,5,6;6″,5″,10″:4',5',6']diisoquino[2,1-a:2',1'-a']
diperimidine-12,25-dione, CAS# 6859-32-1

Bisbenzimidazo[2,1-a:1',2'-b']anthra[2,1,9-def:6,5,10-d'e'f']
diisoquinoline-6,11-dione, CAS# 55034-81-6

Bisbenzimidazo[2,1-a:2',1'-a']anthra[2,1,9-def:6,5,10-d'e'f']
diisoquinoline-10,21-dione, CAS# 55034-79-2

C.I. Pigment red 122, C.I. 73915, CAS# 980-26-7

The obtained novel solubilized vat dyes have chemical structures according to formulae (I)-(X) illustrated in scheme 7:

Scheme 7 solubilized Pigment Violet 19 according to formula (I):

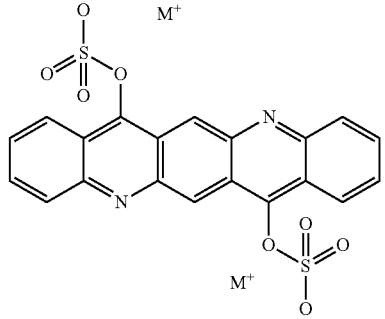

(I)

solubilized Pigment Red 122 according to formula (II):

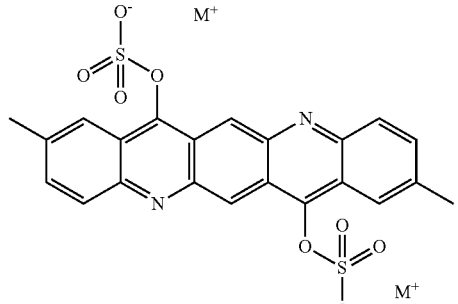

(II)

solubilized Pigment Red 194 according to formula (III):

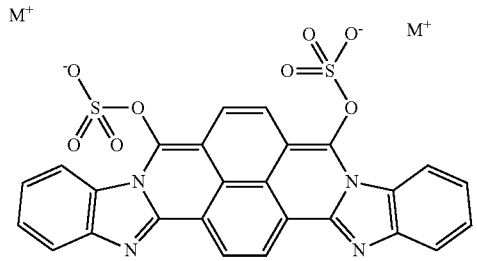

(III)

solubilized Pigment Orange 43 according to formula (IV):

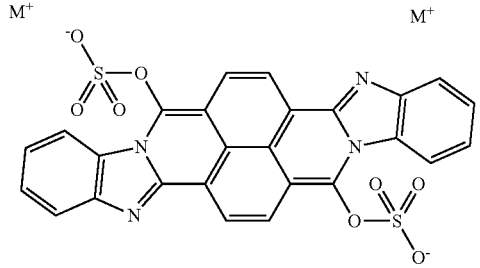

(IV)

-continued solubilized tetraazaviolanthron-trans-black according to formula (V):

(V)

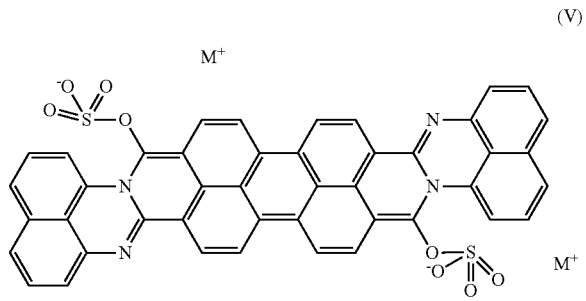

solubilized tetraazaviolanthron-cis-black according to formula (VI):

(VI)

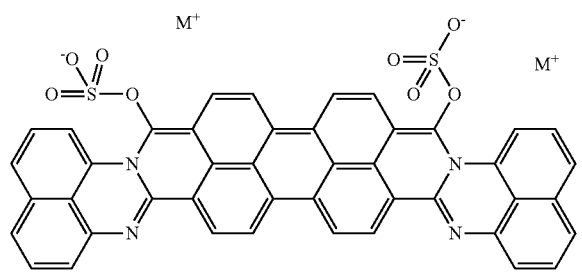

solubilized perylene-amidine-trans-blue according to formula (VII):

(VII)

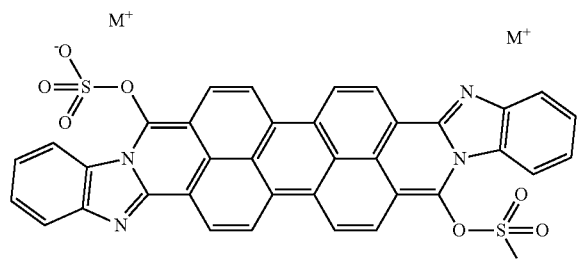

solubilized perylene-amidine-cis-blue according to formula (VIII):

(VIII)

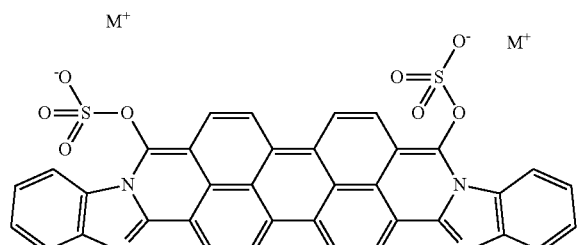

solubilized naphthaline-amidine-trans-blue according to formula (IX):

(IX)

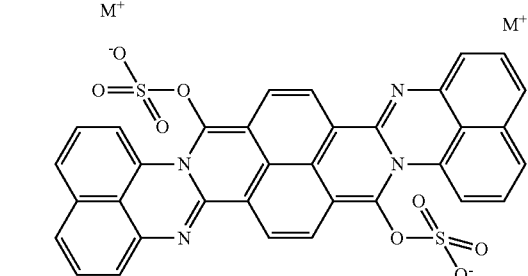

solubilized naphthaline-amidine-cis-blue according to formula (X):

(X)

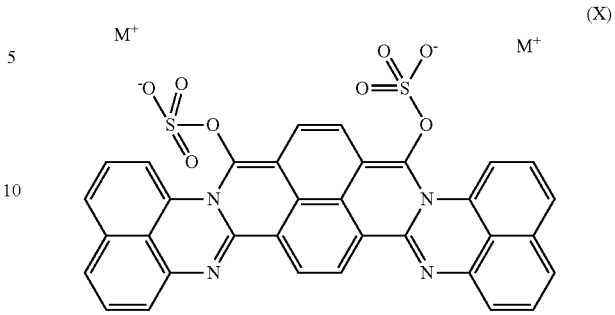

2 the Composition for Coloring a Keratinous Substrate

According to another aspect, the present invention provides a composition for coloring a keratinous substrate. The composition comprises an aqueous medium and a solubilized vat dye dissolved in said medium, wherein said solubilized vat dye is a leuco vat dye sulfuric ester. The vat dye from which the sulfuric ester is derived is preferably selected from anthracene dyes, anthraquinone dyes, naphthalene dyes, violanthrone dyes, tetraaza-violanthrone dyes, acridine dyes, pyrene dyes, dibenzo[a,h]pyrenes, perylene dyes, terrylene dyes, quaterrylene dyes. The composition is essentially free of oxidative dye precursors selected from primary intermediates and couplers, and preferably is free of oxidative dye precursors selected from primary intermediates and couplers. Further, the composition preferably is essentially free of reducing agents capable of forming an enediol, more preferably is free of reducing agents capable of forming an enediol. In addition, the composition preferably is essentially free of sulfur-containing nucleophiles, more preferably is free of sulfur-containing nucleophiles.

According to embodiments, the composition is free of reducing agents. According to other embodiments, the composition comprises a reducing agent. If present, the reducing agent preferably is selected from sulfites, pyrosulfites, dithionites, thiosulfates, or a combination thereof. Further, if present, the reducing agent or combination of reducing agents typically is present in an amount of 0.01-2.0% by weight, preferably in an amount of 0.05-1.0% by weight, based on the weight of the ready-to-use composition.

According to embodiments, the composition is essentially free (or preferably is free) of an at least bifunctional Brönsted base of the general formula X—R—Y, wherein X and Y are proton-accepting groups, and R is an organic moiety comprising 1-20 carbon atoms, 0-5 oxygen atoms and 0-5 nitrogen atoms, the at least bifunctional Brönsted base of the general formula X—R—Y having a molecular mass below 500 g/mol.

According to embodiments, the composition is essentially free (or preferably is free) of diamines, aromatic amines, aromatic phenols, or a combination thereof. In particular, the composition preferably is essentially free (or preferably is free) of aromatic phenols selected from naphthols, resorcinols, and aminophenols. According to embodiments, the composition is essentially free (or preferably is free) of pigments, parabens, silicones, or a combination thereof.

According to embodiments, the composition comprises more than one solubilized vat dye. For example, the composition may comprise two or more, such as three or more leuco vat dye sulfuric esters.

According to embodiments, the solubilized vat dye in the composition is selected from anthracene dyes, naphthalene dyes, violanthrone dyes, tetraaza-violanthrone dyes, acridine dyes, pyrene dyes, dibenzo[a,h]pyrenes, perylene dyes, terrylene dyes, quaterrylene dyes, or a combination thereof. According to preferred embodiments, the solubilized vat dye is selected from naphthalene dyes, violanthrone dyes, tetraaza-violanthrone dyes, acridine dyes, perylene dyes, terrylene dyes, quaterrylene dyes, or a combination thereof. According to particular embodiments, the solubilized vat dye is selected from naphthalene dyes, tetraaza-violanthrone dyes, acridine dyes, perylene dyes, or a combination thereof.

Specific examples of solubilized vat dyes that may be present in the composition are solubilized vat blue 4 (CAS #747-19-5), solubilized vat violet 1 (CAS #1324-57-8), solubilized vat yellow 4 (CAS #3564-70-3), solubilized vat green 1 (CAS #2538-84-3), solubilized vat yellow 1 (CAS #6487-09-8), solubilize vat red 34 (CAS #12226-70-9), solubilized vat red 10 (CAS #10126-90-6), solubilized vat orange 9 (CAS #70356-06-8), solubilized vat orange 3 (CAS #10290-03-6), solubilized vat blue 6 (CAS #2519-28-0), solubilized vat yellow 7 (CAS #3956-62-5), solubilized vat brown 1 (CAS #23725-15-7), solubilized vat blue 20, or a combination thereof. In particular, solubilized vat dyes that may be present in the composition are solubilized vat violet 1 (CAS #1324-57-8), solubilized vat green 1 (CAS #2538-84-3), solubilized vat yellow 1 (CAS #6487-09-8), solubilize vat red 34 (CAS #12226-70-9), solubilized vat orange 9 (CAS #70356-06-8), solubilized vat orange 3 (CAS #10290-03-6), solubilized vat blue 20, or a combination thereof.

According to embodiments, the composition may comprise one or more of the novel solubilized vat dyes according to the present disclosure, according to Formulae (I)-(X):

solubilized Pigment Violet 19 according to formula (I):

(I)

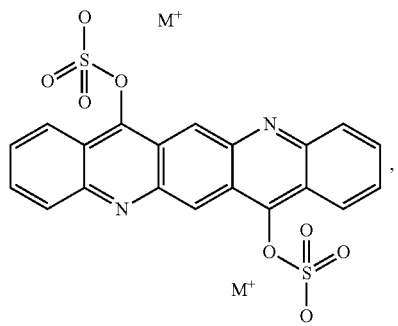

solubilized Pigment Red 122 according to formula (II):

(II)

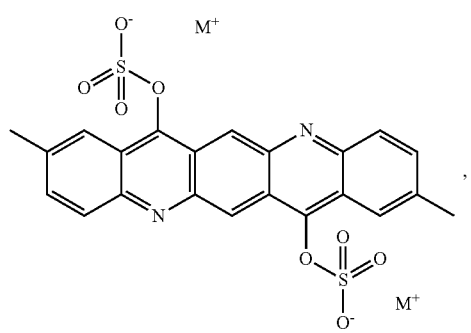

solubilized Pigment Red 194 according to formula (III):

(III)

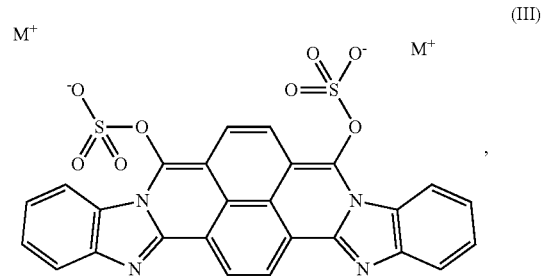

solubilized Pigment Orange 43 according to formula (IV):

(IV)

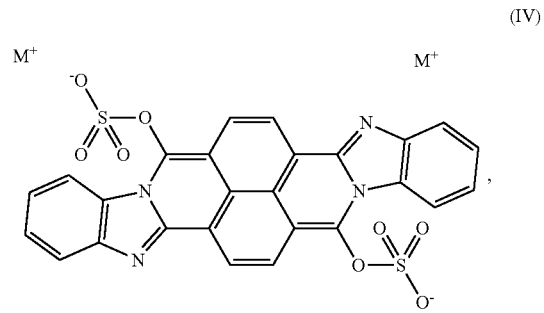

solubilized tetraazaviolanthron-trans-black according to formula (V):

(V)

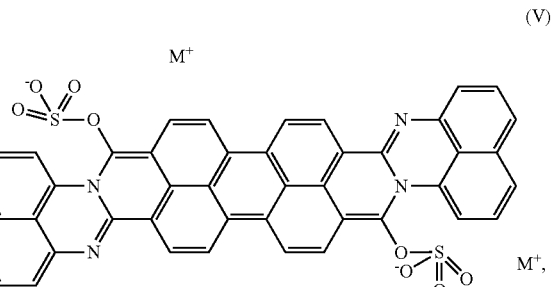

solubilized tetraazaviolanthron-cis-black according to formula (VI):

(VI)

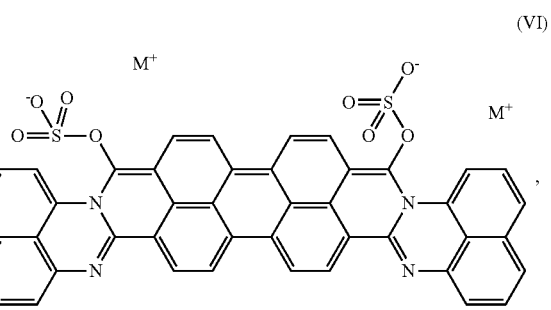

solubilized perylene-amidine-trans-blue according to formula (VII):

(VII)

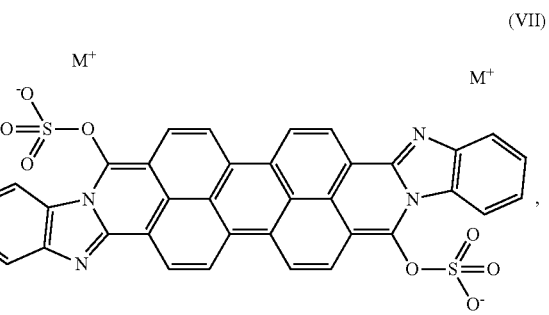

solubilized perylene-amidine-cis-blue according to formula (VIII):

(VIII)

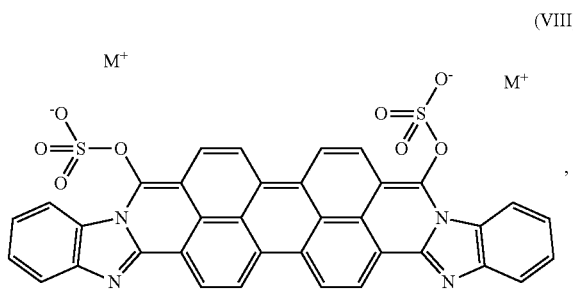

solubilized naphthaline-amidine-trans-blue according to formula (IX):

(IX)

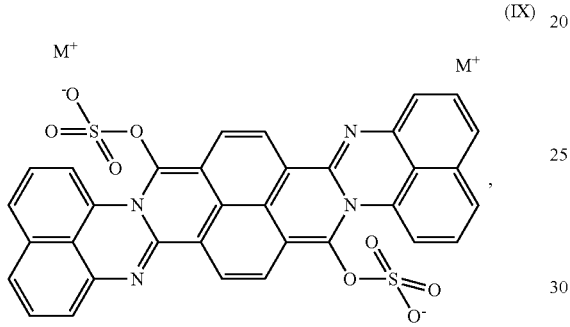

solubilized naphthaline-amidine-cis-blue according to formula (X):

(X)

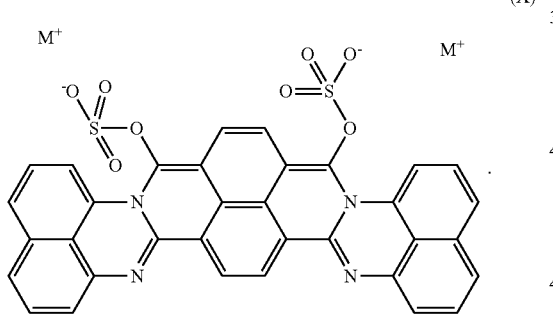

According to specific embodiments, the solubilized vat dye is selected from solubilized vat blue 4 (CAS #747-19-5), solubilized vat blue 6 (CAS #2519-28-0), solubilized vat blue 20, solubilized perylene-amidine-trans-blue according to Formula (VII):

(VII)

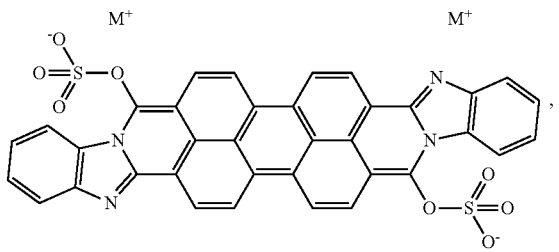

solubilized perylene-amidine-cis-blue according to Formula (VIII):

(VIII)

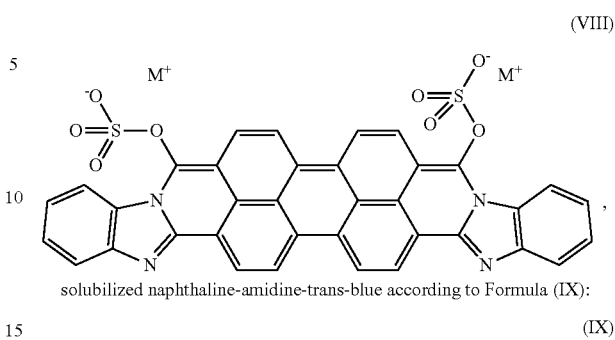

solubilized naphthaline-amidine-trans-blue according to Formula (IX):

(IX)

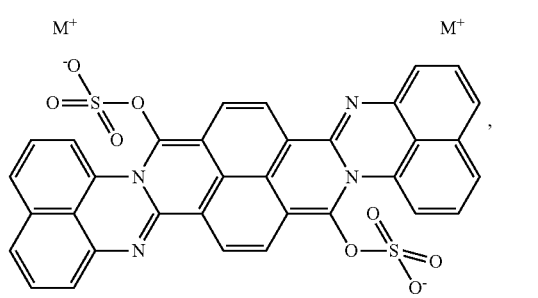

solubilized naphthaline-amidine-cis-blue according to Formula (X):

(X)

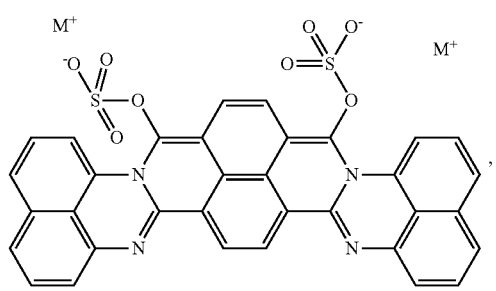

or a combination thereof. A composition comprising one or more of the above solubilized vat dyes is particularly preferable where it is intended to use the composition for correcting a brassy color shade or hue of hair. It is especially useful for correcting a brassy color shade or hue of lifted human scalp.

The composition for coloring a keratinous substrate according to the present invention comprises an aqueous medium. The medium of the composition may be water alone, or water in mixture with a volatile polar protic or aprotic organic solvent. In general, the medium is an aqueous solvent suitable for dissolving the solubilized vat dyes. In addition to water present in the medium, a volatile solvent may be present including a volatile polar protic or aprotic organic solvent. Volatile organic solvents of which non-limiting mention may be made include: volatile pyrrolidones such as 1-methylpyrrolidin-2-one, volatile $C_1$-$C_4$ alkanols such as methanol, ethanol or isopropanol; esters of liquid $C_2$-$C_6$ acids and of volatile $C_1$-$C_8$ alcohols such as methyl acetate, n-butyl acetate, ethyl acetate, propyl acetate, iso-pentyl acetate, or ethyl 3-ethoxypropionate; ketones that are liquid at room temperature and volatile, such as methyl ethyl ketone, methyl isobutyl ketone, diisobutyl ketone, iso-phorone, cyclohexanone, or acetone; volatile polyols such as ethylene glycol and propylene glycol.

It is a particular advantage of the present invention that the composition, and accordingly also the medium of the composition, may be essentially free of organic solvents. If an organic solvent is included, it is preferably selected from ethanol, isopropanol, acetone, and isododecane, or a combination thereof.

The medium may be present in the composition according to the present disclosure in an amount ranging from about 80.0% to about 98.0% by weight, such as from about 88.0% to about 96.0% by weight, for example ranging from 90.0% to 94.0% by weight relative to the total weight of the ready-to-use composition.

Vice versa, where the composition comprises one solubilized vat dye, the solubilized vat dye may be present in the composition according to the present disclosure in an amount ranging from about 0.1% to about 5.0% by weight, such as from about 0.2% to about 2.0% by weight, for example ranging from 0.5% to 1.0% by weight relative to the total weight of the ready-to-use composition.

Where the composition comprises more than one solubilized vat dye, each solubilized vat dye may be present in the composition according to the present disclosure in an amount ranging from about 0.1% to about 5.0% by weight, such as from about 0.2% to about 2.0% by weight, for example ranging from 0.5% to 1.0% by weight relative to the total weight of the ready-to-use composition. The total amount of solubilized vat dyes present in the composition according to the present disclosure preferably does not exceed 7.5% by weight, and more preferably does not exceed 6.0% by weight relative to the total weight of the ready-to-use composition.

The composition has a pH within a range wherein the solubilized vat dyes are stable against degradation. In particular, the composition has an alkaline pH, preferably a pH within the range of from 8.0-10.0. According to embodiments, the composition has a pH in the range of from 8.5-9.5, for example 8.7-9.2.

The composition may comprise further components in addition to the solubilized vat dye(s) and the medium. According to embodiments, the composition further comprises one or more penetration enhancers. Suitable penetration enhancers comprise, for example, ammonia, urea and monoethanolamine. Penetration enhancers typically are present in amounts ranging from ranging from about 5% to about 50% by weight, such as from about 10% to about 40% by weight, for example ranging from 15% to 30% by weight relative to the total weight of the ready-to-use composition.

The composition may further comprise one or more components selected from chelating agents, pH adjusters, fragrances, direct dyes, care components, texture ingredients, medium reagents, solvents, and surfactants. Chelating agents, pH adjusters and fragrances usually will be present in amounts less than 1.0% by weight, typically less than 0.5% by weight relative to the total weight of the ready-to-use composition. Direct dyes, care components, texture ingredients, medium reagents, solvents, and surfactants usually will be present in amounts less than 2.0% by weight, typically less than 1.0% by weight relative to the total weight of the ready-to-use composition. Overall, such components usually may be present in a cumulative amount of 8.0% by weight or less, more typically 5.0% by weight or less relative to the total weight of the ready-to-use composition.

The composition for coloring a keratinous substrate according to the present disclosure is particularly intended for coloring mammalian hair, and preferably for coloring human scalp.

3 The Method for Coloring a Keratinous Substrate

According to an aspect, the present invention provides a method for coloring a keratinous substrate. The method for coloring a keratinous substrate comprises at least steps a1 and b1. Step a1 comprises applying a composition A to the keratinous substrate, said composition A comprising an aqueous medium and a solubilized vat dye dissolved in said medium. The solubilized vat dye is a leuco vat dye sulfuric ester, and composition A is essentially free of oxidative dye precursors selected from primary intermediates and couplers. Step b1 comprises applying a composition B to said keratinous substrate, said composition B having a pH in the range of 3.0-5.0.

Step a1 is carried out prior to step b1. Further, step a1 is carried out under conditions where the leuco vat dye sulfuric esters are stable against hydrolysis. Finally, step a1 is carried out long enough so that the solubilized vat dye has sufficient time to diffuse to a localization on or within the keratinous substrate where the final oxidized vat dye shall be precipitated. In the case of hair dyeing, the solubilized vat dye(s) is/are allowed to penetrate into the cortex of hair at pH 9.0 for 10-40 minutes at 35-40° C., preferably 20-30 minutes at about 37° C. Penetration may be enhanced by the presence in composition A of penetration enhancers, such as ammonia, urea, monoethanolamine, or a combination thereof.

Step b1 is carried out under conditions where the leuco vat dye sulfuric esters are hydrolyzed to the leuco form of the vat dye. Further, step b1 is carried out long enough so that the leuco vat dye sulfuric esters are hydrolyzed to a sufficient extent. Preferably, step b1 is carried out until at least 90.0%, preferably at least 95.0% and more preferably at least 99.0% of the leuco vat dye sulfuric esters are hydrolyzed. Suitable conditions for step b1 at pH 3.0-3.5 comprise 5-15 minutes at 35-40° C., preferably 8-12 minutes at about 37° C.

The leuco form of the vat dyes resulting from step b1 is susceptible to air oxidation, and a separate oxidation step in order to precipitate the pigment form of the vat dyes accordingly is not required. The final color obtained in the method according to the present disclosure is obtained only after the oxidation of the leuco form of the vat dyes resulting from step b1 to the pigment form of the vat dyes. In the case of hair dyeing, air oxidation usually takes about 40-60 minutes for completion, meaning that after the 40-60 minutes any further color change usually is easily not discernable for the naked eye.

In cases where an accelerated result might be preferable, for example, the method according to the present invention for coloring a keratinous substrate optionally may comprise additional step c1. Step c1 comprises applying a composition C to the keratinous substrate. If included, step c1 is carried out after step b1. Composition C comprises an oxidizing agent at alkaline pH. In the case of hair dyeing, step c1 results primarily in the oxidation of the leuco form of the vat dyes, and simultaneously may or may not result in lifting of the hair due to oxidation of the natural melanin in the hair. Such optional lifting of hair depends on the oxidizing agent used in composition C, and lifting the color of the hair over several levels is possible. Suitable conditions for step c1 at pH 9.0 comprise 15-30 minutes at 35-40° C., preferably 20-25 minutes at about 37° C.

3.1 Composition A

Composition A in many aspects corresponds essentially to the composition for coloring a keratinous substrate described in Chapter 2 above. Composition A comprises an aqueous medium and a solubilized vat dye dissolved in said medium, wherein said solubilized vat dye is a leuco vat dye sulfuric ester. Composition A is essentially free of oxidative dye precursors selected from primary intermediates and couplers, preferably is free of oxidative dye precursors selected from primary intermediates and couplers.

Composition A further is preferably essentially free of reducing agents capable of forming an enediol, more preferably is free of reducing agents capable of forming an enediol.

According to embodiments, composition A is free of reducing agents. According to other embodiments, composition A comprises a reducing agent. If present, the reducing agent preferably is selected from sulfites, pyrosulfites, dithionites, thiosulfates, or a combination thereof. Further, if present, the reducing agent or combination of reducing agents typically is present in an amount of 0.01-2.0% by weight, preferably in an amount of 0.05-1.0% by weight, based on the weight of the ready-to-use composition A.

Composition A further is preferably essentially free of sulfur-containing nucleophiles, more preferably is free of sulfur-containing nucleophiles.

According to embodiments, composition A is essentially free (or preferably is free) of an at least bifunctional Brönsted base of the general formula X—R—Y, wherein X and Y are proton-accepting groups, and R is an organic moiety comprising 1-20 carbon atoms, 0-5 oxygen atoms and 0-5 nitrogen atoms, the at least bifunctional Brönsted base of the general formula X—R—Y having a molecular mass below 500 g/mol.

According to embodiments, composition A is essentially free (or preferably is free) of diamines, aromatic amines, aromatic phenols, or a combination thereof. In particular, composition A preferably is essentially free (or preferably is free) of aromatic phenols selected from naphthols, resorcinols, and aminophenols. According to embodiments, composition A is essentially free (or preferably is free) of pigments, parabens, silicones, or a combination thereof.

According to embodiments, composition A comprises more than one solubilized vat dye. For example, composition A may comprise two or more, such as three or more leuco vat dye sulfuric esters.

The vat dye in composition A, from which the sulfuric ester is derived, is preferably selected from anthracene dyes, anthraquinone dyes, naphthalene dyes, violanthrone dyes, tetraaza-violanthrone dyes, acridine dyes, pyrene dyes, dibenzo[a,h]pyrenes, perylene dyes, terrylene dyes, quaterrylene dyes.

Further embodiments of composition A regarding the selection of chemical classes of the solubilized vat dye(s), or the presence of specific known and/or solubilized vat dyes are as described in Chapter 2 above in the context of the composition for coloring a keratinous substrate according to the present disclosure.

Further, the medium of composition A, the amounts of solubilized vat dyes, the pH range, the presence of penetration enhancers and/or other components are as described in Chapter 2 above in the context of the composition for coloring a keratinous substrate according to the present disclosure.

3.2 Composition B

Composition B has a pH within a range wherein the leuco vat dye sulfuric esters are susceptible to degradation. In particular, the composition has an acid pH, preferably a pH within the range of from 3.0-4.5. According to embodiments, the composition has a pH in the range of from 3.2-4.0, for example a pH of about 3.5.

In order to provide an acidic milieu, composition B comprises an organic or inorganic acid. Suitable organic acids include, for example, carboxylic acids, sulfonic acids and phosphonic acids. Suitable inorganic acids include, for example, hydrochloric acid, sulfuric acid, boric acid and carbonic acid. According to embodiments, composition B comprises a monofunctional organic or inorganic acid. According to particular embodiments, composition B comprises an acid selected from acetic acid, boric acid, citric acid, tartaric acid, malic acid, maleic acid, fumaric acid, or a combination thereof. For example, composition B may comprise citric acid, malic acid, or a combination thereof.

Otherwise, composition B comprises an aqueous medium. The medium of composition B may be water alone, or water in mixture with a volatile polar protic or aprotic organic solvent. In addition to water present in the medium, a volatile solvent may be present including a volatile polar protic or aprotic organic solvent. Volatile organic solvents of which non-limiting mention may be made include: volatile pyrrolidones such as 1-methylpyrrolidin-2-one, volatile $C_1$-$C_4$ alkanols such as methanol, ethanol or isopropanol; esters of liquid $C_2$-$C_6$ acids and of volatile $C_1$-$C_8$ alcohols such as methyl acetate, n-butyl acetate, ethyl acetate, propyl acetate, isopentyl acetate, or ethyl 3-ethoxypropionate; ketones that are liquid at room temperature and volatile, such as methyl ethyl ketone, methyl isobutyl ketone, diisobutyl ketone, isophorone, cyclohexanone, or acetone; volatile polyols such as ethylene glycol and propylene glycol.

It is a particular advantage of the present invention the composition B, and accordingly also the medium of the composition, may be essentially free of organic solvents. If an organic solvent is included, it is preferably selected from ethanol, isopropanol, acetone, and isododecane, or a combination thereof.

The amount of medium present in composition B is such that the medium together with acid and optional components disclosed below adds to 100%, relative to the total weight of the ready-to-use composition.

Composition B may further comprise one or more components selected from chelating agents, fragrances, care components, texture ingredients, medium reagents, solvents, and surfactants. Chelating agents and fragrances usually will be present in amounts less than 1.0% by weight, typically less than 0.5% by weight relative to the total weight of the ready-to-use composition. Care components, texture ingredients, medium reagents, solvents, and surfactants usually will be present in amounts less than 2.0% by weight, typically less than 1.0% by weight relative to the total weight of the ready-to-use composition. Overall, such components usually may be present in a cumulative amount of 8.0% by weight or less, more typically 5.0% by weight or less relative to the total weight of the ready-to-use composition.

3.3 Composition C

Optional composition C has an alkaline pH and comprises an oxidizing agent. According to embodiments, the pH of composition C is in the range of 8.0-11.0, in particular in the range of 8.5-9.5. According to specific embodiments, the pH of composition C is about 9.0.

The oxidizing agent present in composition C principally may be any oxidizing agent suitable for accelerating the oxidation of the leuco form of the vat dyes to the pigment for of the vat dyes, as compared to air oxidation alone. Suitably, the oxidizing agent in composition C comprises a peroxide, in particular hydrogen peroxide. In the case of hair dyeing, and if simultaneous lifting of the hair is desired, the oxidizing agent in composition C may comprise a persulfate and/or a percarbonate, or a salt thereof. According to hair lifting embodiments of the present disclosure, composition C further may comprise a bleaching enhancer. Examples of bleaching enhancers are $C_{16}$-$C_{24}$ fatty alcohols, cyclamates, and saccharine.

Otherwise, composition C comprises an aqueous medium. The medium of composition C may be water alone, or water in mixture with a volatile polar protic or aprotic organic solvent. In addition to water present in the medium, a volatile solvent may be present including a volatile polar protic or aprotic organic solvent. Volatile organic solvents of which non-limiting mention may be made include: volatile pyrrolidones such as 1-methylpyrrolidin-2-one, volatile $C_1$-$C_4$ alkanols such as methanol, ethanol or isopropanol; esters of liquid $C_2$-$C_6$ acids and of volatile $C_1$-$C_8$ alcohols such as methyl acetate, n-butyl acetate, ethyl acetate, propyl acetate, isopentyl acetate, or ethyl 3-ethoxypropionate; ketones that are liquid at room temperature and volatile, such as methyl ethyl ketone, methyl isobutyl ketone, diisobutyl ketone, isophorone, cyclohexanone, or acetone; volatile polyols such as ethylene glycol and propylene glycol.

It is a particular advantage of the present invention that composition C, and accordingly also the medium of the composition, may be essentially free of organic solvents. If an organic solvent is included, it is preferably selected from ethanol, isopropanol, acetone, and isododecane, or a combination thereof.

The amount of medium present in composition C is such that the medium together with alkalizer, oxidizing agent, optional bleaching enhancer and optional components disclosed below adds to 100%, relative to the total weight of the ready-to-use composition.

Composition C may further comprise one or more components selected from chelating agents, fragrances, care components, texture ingredients, medium reagents, solvents, and surfactants. Chelating agents, and fragrances usually will be present in amounts less than 1.0% by weight, typically less than 0.5% by weight relative to the total weight of the ready-to-use composition. Care components, texture ingredients, medium reagents, solvents, and surfactants usually will be present in amounts less than 2.0% by weight, typically less than 1.0% by weight relative to the total weight of the ready-to-use composition. Overall, such components usually may be present in a cumulative amount of 8.0% by weight or less, more typically 5.0% by weight or less relative to the total weight of the ready-to-use composition.

3.4 Method for Coloring Hair

According to preferred embodiments of the present disclosure, the method for coloring a keratinous substrate is a method for coloring keratinous fibers, and in particular for coloring natural keratinous fibers. The preferred keratinous substrate is mammalian hair, and in particular human scalp.

The method for coloring hair optionally may include any additional treatments of hair done by the stylist, and in particular any treatments done together with or in the context of coloring hair. Such treatments may comprise prior to and/or subsequent to the hair coloring method embodiments according to the present disclosure, shampooing, conditioning, post-treating and/or drying the hair. Further optional treatments include styling the hair, for example perming or straightening the hair.

4 Method for Correcting a Brassy Color Shade or Hue of Hair

According to an aspect, the present invention provides a method for correcting a brassy color shade or hue of hair. The method is particularly suitable for correcting a brassy color shade or hue of lifted mammalian hair such as human scalp. The method for correcting a brassy color shade or hue of hair comprises at least steps a2 and b2. Step a2 comprises applying a composition AA to the keratinous substrate, said composition AA comprising an aqueous medium and a solubilized vat dye dissolved in said medium. The solubilized vat dye is a leuco vat dye sulfuric ester, and composition AA is essentially free of oxidative dye precursors selected from primary intermediates and couplers. Step b2 comprises applying a composition BB to the hair, said composition B having a pH in the range of 3.0-5.0.

The method for correcting a brassy color shade or hue of hair differs from the method for coloring a keratinous substrate described in Chapter 3 above essentially in that:
  the substrate is mammalian hair, in particular human scalp, and
  the leuco vat dye sulfuric ester(s) present in composition AA are derived from vat dyes giving overall a blue or bluish color.

Accordingly:
Step a2 is carried out prior to step b2. Further, step a2 is carried out under conditions where the leuco vat dye sulfuric esters are stable against hydrolysis. Finally, step a2 is carried out long enough so that the solubilized vat dye has sufficient time to penetrate into the cortex of hair at pH 9.0 for 10-40 minutes at 35-40° C., preferably 20-30 minutes at about 37° C. Penetration may be enhanced by the presence in composition AA of penetration enhancers, such as ammonia, urea, monoethanolamine, or a combination thereof.

Step b2 is carried out under conditions where the leuco vat dye sulfuric esters are hydrolyzed to the leuco form of the vat dye. Further, step b2 is carried out long enough so that the leuco vat dye sulfuric esters are hydrolyzed to a sufficient extent. Preferably, step b2 is carried out until at least 90.0%, preferably at least 95.0% and more preferably at least 99.0% of the leuco vat dye sulfuric esters are hydrolyzed. Suitable conditions for step b2 at pH 3.0-3.5 comprise 5-15 minutes at 35-40° C., preferably 8-12 minutes at about 37° C.

The leuco form of the vat dyes resulting from step b2 is susceptible to air oxidation, and a separate oxidation step in order to precipitate the pigment form of the vat dyes accordingly is not required. The final color obtained in the method for correcting a brassy color shade or hue of hair is obtained only after the oxidation of the leuco form of the vat dyes resulting from step b2 to the pigment form of the vat dyes. Air oxidation usually takes about 40-60 minutes for completion, meaning that after the 40-60 minutes any further color change usually is not easily discernable for the naked eye.

In cases where an accelerated result might be preferable, for example, the method for correcting a brassy color shade or hue of hair optionally comprises additional step c2. Step c2 comprises applying a composition CC to the hair. If included, step c2 is carried out after step b2. Composition CC comprises an oxidizing agent at alkaline pH. Since further lifting of the hair usually is not desired for step c2, the oxidizing agent usually will be hydrogen peroxide. In the case simultaneous lifting of the hair due to oxidation of the natural melanin in the hair should be desired, the oxidizing agent present in composition CC may comprise a persulfate and/or a percarbonate, or a salt thereof. Suitable conditions for step c2 at pH 9.0 comprise 5-15 minutes at 35-40° C., preferably 8-12 minutes at about 37° C.

The method may further comprise treatments as described in Chapter 3.4 above, in particular shampooing, conditioning, post-treating and/or drying the hair. Further optional treatments include styling the hair, for example perming or straightening the hair.

4.1 Composition AA

Composition AA corresponds to composition A described in Chapter 3.1 above, except for a specific selection of the solubilized vat dyes, and the amounts thereof. All other embodiments described above in Chapter 3.1 for composition A (or in Chapter 2 for the composition for coloring a keratinous substrate) apply analogously for composition AA.

In order to be suitable for correcting a brassy color shade or hue of hair, composition AA comprises one or more solubilized vat dyes giving overall a blue or bluish color (i.e. a color complementary to a brassy hue).

According to specific embodiments, the solubilized vat dye present in composition AA is selected from solubilized vat blue 4 (CAS #747-19-5), solubilized vat blue 6 (CAS #2519-28-0), solubilized vat blue 20, solubilized perylene-amidine-trans-blue according to Formula (VII):

(VII)

solubilized perylene-amidine-cis-blue according to Formula (VIII):

(VIII)

solubilized naphthaline-amidine-trans-blue according to Formula (IX):

(IX)

-continued
solubilized naphthaline-amidine-cis-blue according to Formula (X):

(X)

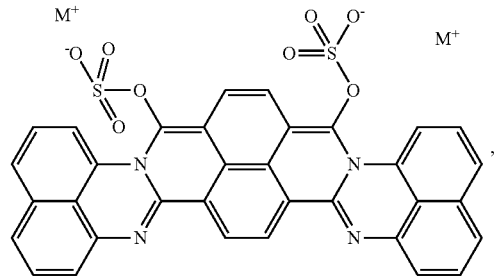

or a combination thereof.

With respect to the amount of solubilized vat dye(s), where composition AA comprises one solubilized vat dye, the solubilized vat dye may be present in composition AA in an amount ranging from about 0.01% to about 0.5% by weight, such as from about 0.02% to about 0.2% by weight, for example ranging from 0.05% to 0.1% by weight relative to the total weight of the composition. Where composition AA comprises more than one solubilized vat dye, each solubilized vat dye may be present in composition AA in an amount ranging from about 0.01% to about 0.5% by weight, such as from about 0.02% to about 0.2% by weight, for example ranging from 0.05% to 0.1% by weight relative to the total weight of the composition. The total amount of solubilized vat dyes present in composition AA preferably does not exceed 0.75% by weight, and more preferably does not exceed 0.6% by weight.

4.2 Composition Bb

Composition BB corresponds to composition B described in Chapter 3.2 above. All embodiments described above in Chapter 3.2 for composition B apply analogously for composition BB.

4.3 Composition Cc

Optional composition CC essentially corresponds to composition C described in Chapter 3.3 above. In particular, composition C has an alkaline pH and comprises an oxidizing agent. According to embodiments, the pH of composition C is in the range of 8.0-11.0, in particular in the range of 8.5-9.5. According to specific embodiments, the pH of composition C is about 9.0.

The oxidizing agent present in composition C principally may be any oxidizing agent suitable for accelerating the oxidation of the leuco form of the vat dyes to the pigment for of the vat dyes, as compared to air oxidation alone. Suitably, the oxidizing agent in composition C comprises a peroxide, in particular hydrogen peroxide. Further, considering that the method for correcting a brassy color shade or hue of hair often will be carried out on hair that had previously been lifted, further lifting of the hair may not be desired. According to embodiments, the method for correcting a brassy color shade or hue of hair often will be carried out on bleached hair. Nevertheless, in case further lifting of the hair should be intended, the oxidizing agent in composition CC may comprise a persulfate and/or a percarbonate, or a salt thereof, and optionally a bleaching enhancer.

The medium of composition CC, and optional additional components of composition CC are as described in Chapter 3.3 above in the context of composition C.

5 Method for Changing the Color of a Vat-Dye-Colored Keratinous Substrate

According to an aspect, the present invention provides a method for changing the color of a keratinous substrate which previously had been colored with a vat dye or a combination of more than one vat dye. According to embodiments, the method is for changing the color of a keratinous substrate colored by the method according to the present invention for coloring a keratinous substrate. According to embodiments, the method is a method for changing the color of hair colored or corrected by a method according to the present invention.

The method comprises applying to the keratinous substrate a composition D. Composition D has a pH in the range of 11.0-12.0, in particular a pH of about 11.5.

Composition D further comprises a reducing agent or a combination of reducing agents. According to embodiments, the reducing agent or combination of reducing agents is capable of forming an enediol. For example, the reducing agent may be selected from monohydroxy acetone, dihydroxy acetone, 3-hydroxy-2-butanone, 2-hydroxycyclohexane-1-one, glycolaldehyde, 2-hydroxy-1,2-diphenylethan-1-one, 1,5-dihydroxy-pentan-2-one, 2,3-dihydroxy-acrylaldehyde, 2,3-dihydroxy-cyclopentan-1-one, or a combination thereof. The reducing agent or combination of reducing agents is present in the ready-to-use composition D in an amount of in an amount of 5.0-20.0% by volume, preferably 8-15.0% by volume, such as 10.0-12.0% by volume.

The reducing agent in composition D is able at the rather harsh alkaline conditions to convert any vat dyes present on or in the keratinous substrate to the corresponding soluble leuco form, which soluble form then may be washed out. After applying to the hair, composition D is left on the keratinous substrate for 40-80 minutes at 30-50° C. and subsequently rinsed. For decoloring mammalian hair, composition D is left on the hair, in particular human scalp for 40-80 minutes such as about 60 minutes at 30-40° C., in particular 37° C., subsequently rinsed with water, typically followed by shampooing, optional treatment with a conditioner, and blow-drying.

Composition D may further comprise one or more components selected from chelating agents, fragrances, care components, texture ingredients, medium reagents, solvents, and surfactants. Chelating agents, and fragrances usually will be present in amounts less than 1.0% by weight, typically less than 0.5% by weight relative to the total weight of the ready-to-use composition. Care components, texture ingredients, medium reagents, solvents, and surfactants usually will be present in amounts less than 2.0% by weight, typically less than 1.0% by weight relative to the total weight of the ready-to-use composition. Overall, such components usually may be present in a cumulative amount of 8.0% by weight or less, more typically 5.0% by weight or less relative to the total weight of the ready-to-use composition.

Besides alkalizer, reducing agent, and optional components, composition D is made up of an aqueous medium. The medium of composition D may be water alone, or water in mixture with a volatile polar protic or aprotic organic solvent. In addition to water present in the medium, a volatile solvent may be present including a volatile polar protic or aprotic organic solvent. Volatile organic solvents of which non-limiting mention may be made include: volatile pyrrolidones such as 1-methylpyrrolidin-2-one, volatile $C_1$-$C_4$ alkanols such as methanol, ethanol or isopropanol; esters of liquid $C_2$-$C_6$ acids and of volatile $C_1$-$C_8$ alcohols such as methyl acetate, n-butyl acetate, ethyl acetate, propyl acetate, isopentyl acetate, or ethyl 3-ethoxypropionate; ketones that are liquid at room temperature and volatile, such as methyl ethyl ketone, methyl isobutyl ketone, diisobutyl ketone, isophorone, cyclohexanone, or acetone; volatile polyols such as ethylene glycol and propylene glycol.

It is a particular advantage of the present invention that composition D, and accordingly also the medium of the composition, may be essentially free of organic solvents. If an organic solvent is included, it is preferably selected from ethanol, isopropanol, acetone, and isododecane, or a combination thereof.

6 The Kit

According to an aspect, the present invention provides a kit for coloring a keratinous substrate. In particular, the kit may be for coloring a keratinous fiber such as mammalian hair, in particular human scalp.

The kit comprises a first compartment (also denoted herein as compartment A) comprising a leuco vat dye sulfuric ester or salt thereof. According to embodiments, the first compartment comprises a mixture of two or more leuco vat dye sulfuric esters or salts thereof, for example three of four leuco vat dye sulfuric esters or salts thereof. The kit further comprises a second compartment (also denoted herein as compartment B) comprising an acid or salt thereof. According to embodiments, the second compartment comprises a monofunctional organic or inorganic acid, or salt thereof. According to particular embodiments, the second compartment comprises an acid selected from acetic acid, boric acid, citric acid, tartaric acid, malic acid, maleic acid, fumaric acid, a salt thereof, or a combination thereof. For example, the second compartment may comprise citric acid, malic acid, a salt thereof, or a combination thereof.

According to embodiments, the kit further comprises a third compartment (also denoted herein as compartment C) comprising an oxidizing agent. According to embodiments, the third compartment comprises a peroxide, such as for example hydrogen peroxide. Alternative or in addition to the peroxide, the third compartment comprises a persulfate and/or a percarbonate, or a salt thereof.

According to embodiments, the kit further comprises a bleaching enhancer. The bleaching enhancer may be present in the third compartment, or provided in a separate compartment.

According to embodiments, the kit further comprises a fourth compartment (also denoted herein as compartment D) comprising a reducing agent or a combination of reducing agents. According to embodiments, the reducing agent or combination of reducing agents is capable of forming an enediol. For example, the reducing agent may be selected from monohydroxy acetone, dihydroxy acetone, 3-hydroxy-2-butanone, 2-hydroxycyclohexane-1-one, glycolaldehyde, 2-hydroxy-1,2-diphenylethan-1-one, 1,5-dihydroxy-pentan-2-one, 2,3-dihydroxy-acrylaldehyde, 2,3-dihydroxy-cyclopentan-1-one, or a combination thereof.

Generally, the contents of the respective compartments of the kit may be present in solid form or in semi-solid form or in liquid form. The term "solid form" as used in this context denotes powders and similar essentially dry physical forms, which will be mixed with water or a medium prior to use. The term "semi-solid form" as used in this context denotes pastes and similar non-flowing concentrated physical forms, which will be mixed with water or a medium prior to use. The term "liquid form" as used in this context denotes the ready-to-use form, which does not require mixing with water or a medium prior to use.

According to embodiments wherein the contents of one or more compartments of the kit are present in solid form or in semi-solid form, the kit may further comprise one or more compartments comprising media for mixing with the contents of one or more compartments. Accordingly, the kit may further comprise:

- a compartment comprising a medium which upon mixing with the contents of compartment A is capable of forming the composition for coloring a keratinous substrate according to the present disclosure (or composition A or composition AA, respectively), and/or
- a compartment comprising a medium which upon mixing with the contents of compartment B is capable of forming composition B or composition BB, respectively, according to the present disclosure, and/or
- a compartment comprising a medium which upon mixing with the contents of compartment C is capable of forming composition C or composition CC, respectively, according to the present disclosure, and/or
- a compartment comprising a medium which upon mixing with the content of compartment D is capable of forming a composition for changing the color of a keratinous substrate which previously had been colored with a vat dye or a combination of more than one vat dye (composition D) according to the present disclosure.

According to embodiments wherein the contents of one or more compartments of the kit are present in liquid form, the respective compartments comprise the ready-to use compositions, which obviously already comprise (optional and) all required ingredients to form compositions A/AA, B/BB, C/CC and/or D according to the present disclosure as described in Chapters 3-5 above.

Further as noted in Chapters 3-5 above, the composition for coloring a keratinous substrate (or composition A or composition AA, respectively) is, or preferably is essentially free of certain compounds. According to embodiments, the said composition is, or preferably is free of certain compounds. Analogous considerations apply to the contents of compartment A, and any media for mixing with the contents of compartment A.

According to further embodiments, the kit may further comprise at least one compartment comprising one or more leuco vat dye sulfuric esters, or salts thereof, resulting overall in a color different from the one provided by the leuco vat dye sulfuric ester(s) in compartment A. Again, the contents of such further compartment(s) may be present in solid form or in semi-solid form or in liquid form. The presence of such further vat-dye-containing compartment(s) may allow the stylist to further individualize the color to the wishes of the customer.

7 Novel Solubilized Vat Dyes, Uses Thereof and Substrates Having Adsorbed the Novel Solubilized Vat Dyes According to another aspect, the present invention provides novel leuco vat dye sulfuric esters, which previously had not been disclosed in the art. The novel leuco vat dye sulfuric esters, corresponding to Formulae (I) through (X), are denoted herein as follows:

Solubilized Pigment Violet 19 according to formula (I):

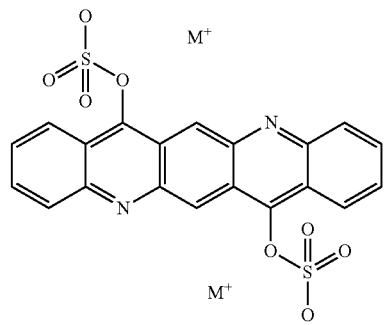

(I)

Solubilized Pigment Red 122 according to formula (II):

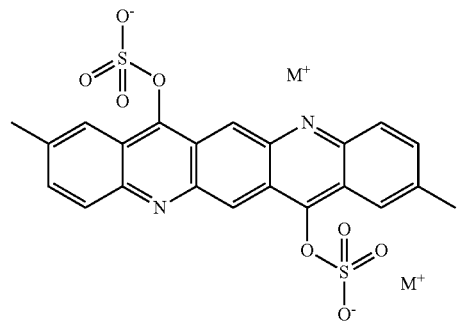

(II)

Solubilized Pigment Red 194 according to formula (III):

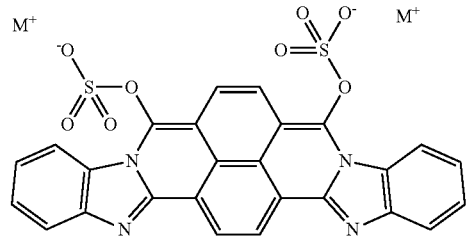

(III)

Solubilized Pigment Orange 43 according to formula (IV):

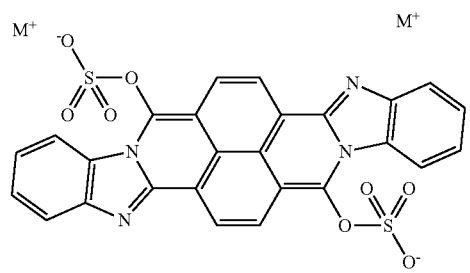

(IV)

Solubilized tetraazaviolanthron-trans-black according to formula (V):

(V)

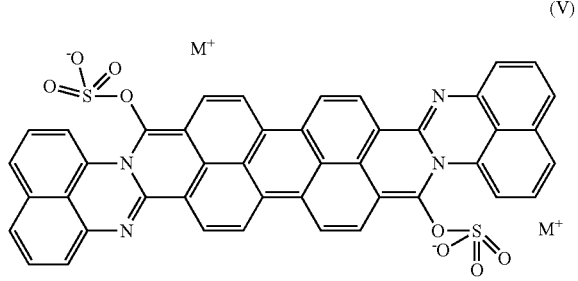

-continued

Solubilized tetraazaviolanthron-cis-black according to formula (VI):

(VI)

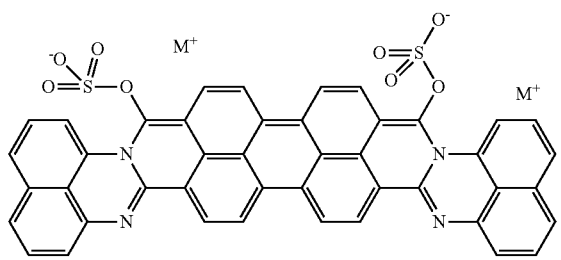

Solubilized perylene-amidine-trans-blue according to formula (VII):

(VII)

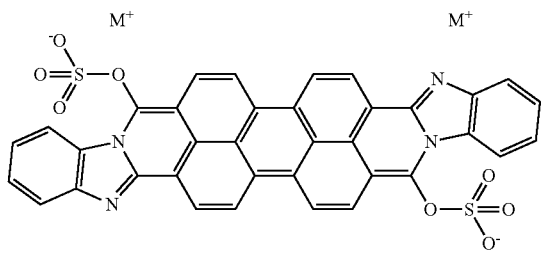

Solubilized perylene-amidine-cis-blue according to formula (VIII):

(VIII)

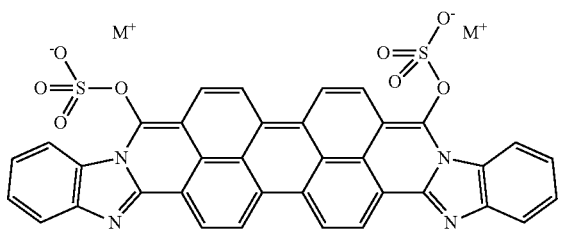

Solubilized naphthaline-amidine-trans-blue according to formula (IX):

(IX)

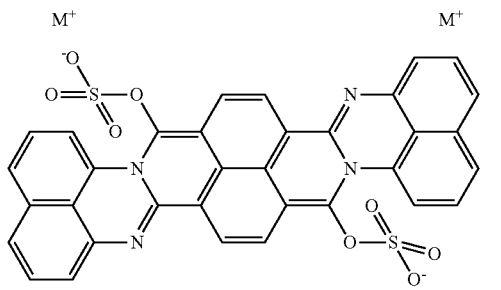

Solubilized naphthaline-amidine-cis-blue according to formula (X):

(X)

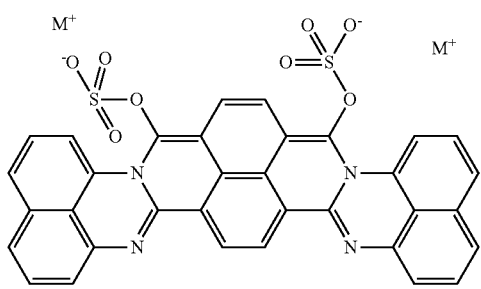

According to another aspect, the present invention provides using the leuco vat dye sulfuric esters according to Formulae (I) through (X) in a vat dyeing process. In particular, the present disclosure contemplates using the leuco vat dye sulfuric esters according to Formulae (I) through (X) for coloring a keratinous substrate. According to preferred embodiments, the present disclosure contemplates using the leuco vat dye sulfuric esters according to Formulae (I) through (X) for coloring mammalian hair, in particular human scalp.

According to another aspect, the present invention provides substrates having adsorbed thereto a leuco vat dye sulfuric ester according to the above Formulae (I) through (X), or a combination thereof. According to embodiments, the substrate is a fiber. According to embodiments, the substrate is a keratinous substrate. For example, the substrate may be a keratinous fiber. According to a particular embodiment, such keratinous fiber may be mammalian hair such as human scalp. According to other embodiments, such keratinous fiber may be a natural fiber such as wool or silk.

According to still other embodiments, the substrate may be a cellulosic substrate. For example, the substrate may be selected from natural and/or manufactured cellulosic fibers. Natural cellulosic fibers encompass, for example, cotton and linen fibers. Manufactured cellulosic fibers encompass, for example, rayon and viscose fibers.

8 Examples

The coloring method described in the following examples, which method uses solubilized vat dyes, comprises the steps of applying leuco vat dye sulfuric esters, hydrolyzing the leuco vat dye sulfuric esters to the leuco form, and actively oxidizing the leuco form to the respective insoluble pigment form of the vat dyes.

A Penetration of the Solubilized Vat Dyes into the Hair Cortex.

Penetration occurs under mild alkaline conditions at pH=9 in the presence of ammonia or other penetration enhancers such as urea. At this point in time it is important to keep the sulfuric ester structure intact to avoid any early oxidation of the solubilized vat dye as this will distract the penetration process and will lead to incomplete use of the applied dye amount which will result in an unsatisfactory color result. In order to prevent the solubilized vat dyes to start the oxidation at that point in time, sodium sulfite as reducing agent may be added to the coloring mixture. Addition of sodium meta bisulfite as described in U.S. Pat. No. 5,364,415 (Lewis et. al.), to lower the alkaline pH given by the addition of ammonia or urea down to pH=6 is not beneficial as it will hinder the solubilized vat dye to penetrate, and will decrease the swelling of the keratin fiber which needs mild alkaline conditions. Hence, the adjustment to a gentle acidic pH needs to start no earlier before the penetration is completed to properly allow the bulky aromatic chromophore systems to deeply flow into the cortex of the swollen hair.

B Adjusting the pH to Gentle Acidic Conditions

The alkaline dyeing solution is then treated with, for example, acetic acid, ascorbic acid, boric acid or citric acid to adjust the pH to mildly acidic, for example pH 3.0-3.5. This pH change will trigger hydrolysis of the sulfuric ester to yield the free vat acid (leuco form). This process typically will require no more than 10 min, after which time the solubilized vat dye esters are completely hydrolyzed. At that point in time the leuco form has reached the maximum sensitivity to oxidizers.

C Oxidation for Precipitating the Insoluble Pigments into the Cortex of the Hair The hair is briefly rinsed with water to remove any excess remaining dye material from the surface of the hair. After that, any oxidizing procedure can be applied. This includes very gentle conditions using hydrogen peroxide solutions from 1-12% by volume. Common in the hair color industry are the following typical concentrations: 1.9, 6, 9 or 12% by volume. Hydrogen peroxide can be applied also together with bleaching agents such as sodium/potassium/ammonium persulfate or percarbonates. The oxidation to convert the leuco form to the vat dye pigments is typically completed within 20 min. Simultaneously lifting of the hair (oxidizers keep also oxidizing natural melanin in the hair) will be completed within the same time frame. Hence, the overall treatment will last no longer than 1 h which does correspond well to current oxidative hair coloring applications, with no increase of any complexity of the treatment. A significant advantage is that any formulations can totally skip the use of organic solvents and alcohols such as ethanol or iso-propyl-alcohol. In addition, considering that all solubilized vat dyes exhibit an absolutely comparable behavior regarding homogeneous dye take-up and general fastness properties, all solubilized vat dyes can be easily blended with each other so that formulators may create all kind of natural and fashionable shades without any limits.

D General Procedure 2 g urea (penetration enhancer), 200 mg sodium sulfite (reducing agent) and 120 mg of the respective solubilized vat dye (color component) are dissolved in 15 ml water. This simple mixture is already sufficient to obtain the desired colorations on hair. In principal, all additional components which are a typical ingredients of an oxidative hair coloring system in addition to the above-mentioned components can be applied as well with no exception and without negative impact on the coloring result. This includes the following ingredient groups: coloring agents (solubilized vat dyes), penetration enhancers/alkalizers (e.g. ammonia, urea), reducing agents/radical scavengers (e.g. sodium sulfite etc.), chelating agents (e.g. EDTA, EDDS, editronic acid) etc.), fragrances, care components (e.g. hydrolyzed keratin, dimethicone, polyquaternium types etc.) texture ingredients (e.g. carbomer, cocoamide, hydroxyethyl cellulose etc.), medium reagents (e.g. cetearyl alcohol, lanolin alcohol, glycerin stearate etc.) and surfactants (e.g. laurylether sulfate, lauryl sulfo acetate etc.).

This aqueous solution is heated gently to 40° C. and 1-2 hair switches are placed in the coloring bath for 25-30 min. Subsequently, the hair switches are taken out, put aside, and the solution is treated with acetic acid to achieve a pH at 3.0-3.5 (putting aside the hair switches is only useful in a lab experiment to avoid that the hair switches are felting during the pH change which would make it difficult to separate them at the end of the treatment but is of no concern in real applications on head). The hair switches then are placed back into the vessel and kept there for further 10 min.

Subsequently, the hair switches are taken out and briefly rinsed with water and subsequently placed into an oxidation bath at 40° C., comprising standard commercial products, so called color developers, containing hydrogen peroxide. Typical contents are 1.9, 6, 9 and 12% by volume. The developer can be chosen in absolute freedom depending on the grade of lift one may desire. The oxidation bath may also comprise a hydrogen peroxide containing developer plus a bleaching powder containing typical oxidizers such as sodium, potassium or ammonium persulfates or percarbonates. This treatment will lead to a maximum lift/bleach of the hair including a simultaneous coloration. After 20 min, the hair switches are taken out, rinsed with warm water to completely remove any traces of oxidants, powdered particles etc. and washed with shampoo, followed by a post-treatment with a commercial conditioner, and finally dried with a blow dryer. This post-treatment ensures that the hair cortex will be closed again and the hair is converted back to the original state with a closed and healthy surface.

The following table (scheme 8) summarizes the colorations obtained using different hair types and oxidation levels using the solubilized form of the respective vat dyes on hair switches.

Scheme 8:

| leuco vat dye sulfuric ester in first step | type of hair | oxidation treatment in third step | color result | L a b value* |
|---|---|---|---|---|
| vat yellow 4 | Natural blond | Hydrogen peroxide 9%, pH = 9 | Bright and glossy straw yellow | L = 57.23 a = 21.37 b = 92.50 |
| vat yellow 4 | Natural blond | Hydrogen peroxide 12% plus Blondor powder**, ratio 1:1 | Very intense golden orange-yellow | L = 55.69 a = 36.38 b = 94.63 |
| vat violet 1 | Natural blond | Hydrogen peroxide 9%, pH = 9 | Bright and deeply intense, warm violet | L = 11.14 a = 43.53 b = −27.54 |
| vat violet 1 | Natural blond | Hydrogen peroxide 12% plus Blondor powder**, ratio 1:1 | Bright and deeply intense, warm violet | L = 10.36 a = 41.16 b = −30.35 |
| vat green 1 | Natural brown 5/0 | Hydrogen peroxide 9%, pH = 9 | Warm, deep, mahagony red | L = 2.79 a = 9.74 b = 4.66 |
| vat green 1 | Natural blond | Hydrogen peroxide 9%, pH = 9 | Bright tomato red | L = 31.82 a = 41.46 b = 35.92 |
| vat green 1 | Natural brown 5/0 | Hydrogen peroxide 12% plus Blondor powder** ratio 1:1 | Light green intense | L = 18.28 a = −46.65 b = 11.49 |
| vat green 1 | Natural blond | Hydrogen peroxide 12% plus Blondor powder** ratio 1:1 | Light green intense | L = 22.36 a = −54.90 b = 2.07 |
| vat violet 1 vat yellow 4 ratio 2:1 | Natural brown 5/0 | Hydrogen peroxide 9%, pH = 9 | Warm, intense dark red | L = 5.09 a = 26.17 b = 8.61 |
| vat violet 1 vat yellow 4 ratio 2:1 | Natural blond | Hydrogen peroxide 9%, pH = 9 | Intense wine red | L = 14.20 a = 35.60 b = 21.82 |
| vat green 1 vat yellow 4 ratio 2:1 | Natural blond | Hydrogen peroxide 9%, pH = 9 | Orange-red | L = 35.67 a = 24.70 b = 42.71 |
| vat green 1 vat yellow 4 ratio 2:1 | Natural brown 5/0 | Hydrogen peroxide 9%, pH = 9 | Warm chestnut brown | L = 14.45 a = 17.53 b = 24.70 |
| vat green 1 vat yellow 4 ratio 2:1 | Natural blond | Hydrogen peroxide 12% plus Blondor powder**, ratio 1:1 | Brilliant lawn green | L = 26.51 a = −45.42 b = 35.26 |
| vat green 1 vat yellow 4 ratio 2:1 | Natural brown 5/0 | Hydrogen peroxide 12% plus Blondor powder**, ratio 1:1 | Brilliant lawn green | L = 23.03 a = −38.54 b = 33.21 |

Scheme 8:

| leuco vat dye sulfuric ester in first step | type of hair | oxidation treatment in third step | color result | L a b value* |
|---|---|---|---|---|
| vat green 1 vat yellow 4 ratio 1:1 | Natural blond | Hydrogen peroxide 9%, pH = 9 | Tomato orange-red | L = 24.67 a = 37.56 b = 42.38 |
| vat green 1 vat yellow 4 ratio 1:1 | Natural brown 5/0 | Hydrogen peroxide 9%, pH = 9 | Hazelnut reddish brown | L = 3.10 a = 7.56 b = 5.19 |
| vat green 1 vat yellow 4 ratio 1:1 | Natural blond | Hydrogen peroxide 12% plus Blondor powder**, ratio 1:1 | Bright frog green | L = 12.83 a = −28.96 b = 1.34 |
| vat green 1 vat yellow 4 ratio 1:1 | Natural brown 5/0 | Hydrogen peroxide 12% plus Blondor powder**, ratio 1:1 | Bright frog green | L = 9.30 a = −22.56 b = 15.66 |
| vat violet 1 vat yellow 4 ratio 1:1 | Natural blond | Hydrogen peroxide 9%, pH = 9 | Dark, warm cherry red | L = 5.95 a = 30.06 b = 10.10 |
| vat violet 1 vat yellow 4 ratio 1:1 | Natural blond | Hydrogen peroxide 12% plus Blondor powder**, ratio 1:1 | Dark, warm cherry red | L = 10.16 a = 30.16 b = 17.36 |
| vat violet 1 vat yellow 4 ratio 1:2 | Natural blond | Hydrogen peroxide 9%, pH = 9 | Foxy reddish brown | L = 13.91 a = 35.84 b = 23.72 |
| vat violet 1 vat yellow 4 ratio 1:2 | Natural brown 5/0 | Hydrogen peroxide 9%, pH = 9 | Dark, intense reddish brown | L = 1.56 a = 9.50 b = 2.53 |
| vat violet 1 vat yellow 4 ratio 1:2 | Natural blond | Hydrogen peroxide 12% plus Blondor powder**, ratio 1:1 | Light foxy reddish brown | L = 25.64 a = 28.27 b = 34.80 |
| vat violet 1 vat yellow 4 ratio 1:2 | Natural brown 5/0 | Hydrogen peroxide 12% plus Blondor powder**, ratio 1:1 | Foxy reddish brown | L = 11.59 a = 30.66 b = 19.82 |
| vat violet 1 vat green 1 ratio 1:1 | Natural blond | Hydrogen peroxide 9%, pH = 9 | Intense purple red | L = 6.26 a = 31.38 b = −2.54 |
| vat violet 1 vat green 1 ratio 1:1 | Natural brown 5/0 | Hydrogen peroxide 9%, pH = 9 | Dark brownish purple red | L = 4.46 a = 20.62 b = 3.05 |
| vat violet 1 vat green 1 ratio 1:1 | Natural blond | Hydrogen peroxide 12% plus Blondor powder**, ratio 1:1 | Dark intense blue | L = 2.50 a = 5.70 b = −22.57 |
| vat violet 1 vat green 1 ratio 1:1 | Natural brown 5/0 | Hydrogen peroxide 12% plus Blondor powder**, ratio 1:1 | Dark metal blue | L = 2.77 a = 3.33 b = −18.51 |
| vat violet 1 vat green 1 ratio 1:2 | Natural blond | Hydrogen peroxide 9%, pH = 9 | Intense, light purple red | L = 14.86 a = 38.66 b = −16.58 |
| vat violet 1 vat green 1 ratio 1:2 | Natural brown 5/0 | Hydrogen peroxide 9%, pH = 9 | Chestnut purple brow | L = 6.19 a = 25.04 b = 10.52 |
| vat violet 1 vat green 1 ratio 1:2 | Natural blond | Hydrogen peroxide 12% plus Blondor powder**, ratio 1:1 | Dark, soft blue | L = 10.01 a = 5.46 b = −29.34 |
| vat violet 1 vat green 1 ratio 1:2 | Natural brown 5/0 | Hydrogen peroxide 12% plus Blondor powder**, ratio 1:1 | Dark metal blue | L = 3.46 a = 1.75 b = −18.34 |

*Color difference is measured via standard L a b values:
L = being a measure of lightness and intensity. Range: 0 = black, 100 = white
a = being a measure of red and green tones. Red = positive values, Green = negative values
b = being a measure of blue and yellow tones. Yellow = positive values, Blue = negative values
**Blondor = bleaching powder, comprising peroxodisulfates, commercial brand of the Wella Company ("Wella Professionals")

E Comparison with Commercial Shades, and Color Remanence

Hair switches (natural blond) are colored as described above using the solubilized form of vat yellow 4, or respectively, using commercial color shades in a salon test.

The commercial shades tested are Magma limoncello, and Vidal Sassoon yellow, both commercial brands of the Wella Company ("Wella Professionals"). Color remanence is determined directly after performing the coloration ("fresh ON"), after 5 washes with shampoo and after 10 washes with shampoo.

The following table (scheme 9) summarizes the color obtained using vat yellow 4 or commercial shade Magma limoncello, or commercial shade Vidal Sassoon yellow, respectively.

Scheme 9:

| | vat yellow 4 | | | Magma limoncello | | | Vidal Sassoon yellow | | |
|---|---|---|---|---|---|---|---|---|---|
| L*a*b | L | a | b | L | a | b | L | a | b |
| fresh ON | 67.94 | 10.29 | 39.78 | 68.67 | 4.11 | 25.82 | 70.23 | 8.03 | 49.90 |
| 5 washes | 64.43 | 7.72 | 32.97 | 68.63 | 4.24 | 23.76 | 67.49 | 5.78 | 23.88 |
| 10 washes | 63.68 | 8.73 | 34.77 | 68.92 | 4.83 | 23.90 | 66.44 | 4.14 | 23.53 |

Figure 11A:
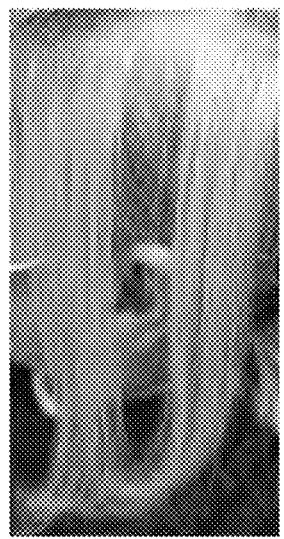
FIG. 11a shows a comparison of the coloration obtained using vat yellow 4 or commercial shade Magma limoncello, respectively, in a salon test directly after having performed the coloration ("fresh ON").
Figure 11B:
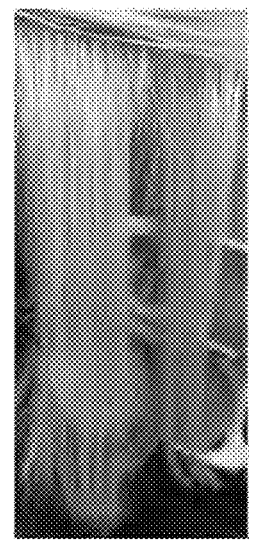
FIG. 11b shows a comparison of the coloration obtained using vat yellow 4 or commercial shade Vidal Sassoon yellow, respectively, in a salon test directly after having performed the coloration ("fresh ON").

The coloration results obtained and the color remanence after 5 and 10 washes with shampoo are shown in FIGS. 11-13:

FIGS. 11a and 11b show the coloration obtained in a salon test directly after having performed the coloration ("fresh ON"), comparing vat yellow 4 with Magma limoncello and Vidal Sassoon yellow.

Figure 12A:
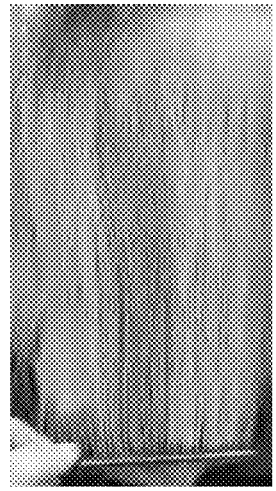
FIG. 12a shows a comparison of the color obtained using vat yellow 4 or commercial shade Magma limoncello, respectively, in a salon test after 5 washes with shampoo.
Figure 12B:
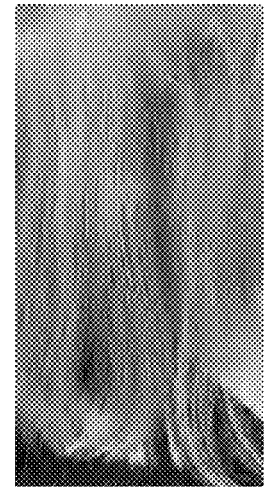
FIG. 12b shows a comparison of the color obtained using vat yellow 4 or commercial shade Vidal Sassoon yellow, respectively, in a salon test after 5 washes with shampoo.

FIGS. 12a and 12b show the color remanence after 5 washes, comparing vat yellow 4 with Magma limoncello and Vidal Sassoon yellow.

Figure 13A:
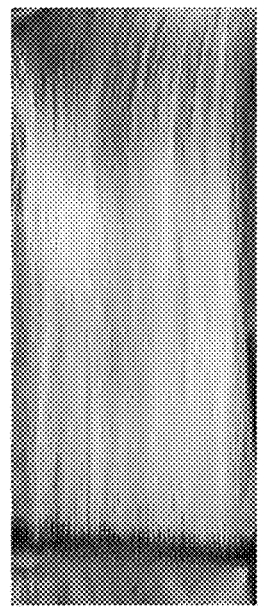
FIG. 13a shows a comparison of the color obtained using vat yellow 4 or commercial shade Magma limoncello, respectively, in a salon test after 10 washes with shampoo.
Figure 13B:
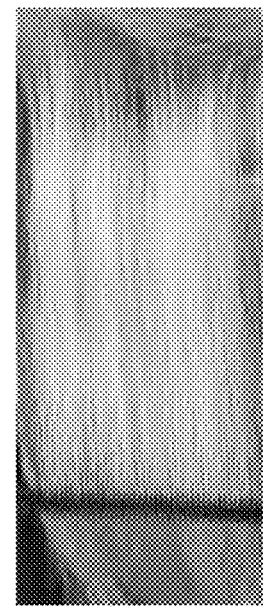
FIG. 13b shows a comparison of the color obtained using vat yellow 4 or commercial shade Vidal Sassoon yellow, respectively, in a salon test after 10 washes with shampoo.

FIGS. 13a and 13b show the color remanence after 5 washes, comparing vat yellow 4 with Magma limoncello and Vidal Sassoon yellow.

F Procedure for Adjusting a Completed Coloration for Correction Purposes 2 g urea are dissolved in 15 ml water. The pH is carefully adjusted to pH=11.5 with 32% caustic soda (NaOH), subsequently 10% by volume of hydroxy-acetone are added slowly and the mixture heated to 40° C. A hair switch, colored with a solubilized and later oxidized vat dye according to the above-mentioned procedure, is placed into this alkaline solution and kept at 40° C. for 1 h while completely covered in the solution. The hair switch is removed, rinsed with water, and washed with shampoo followed by treatment with a commercial conditioner, and finally dried with a blow dryer. The remaining alkaline solution turns significantly colored caused by removal of the respective vat dye. The color that faded out from the hair switches depends on the dye used previously for the coloration of the hair switch.

The following table (scheme 10) summarizes the color obtained using vat violet 1 or vat yellow 4, respectively, and the correction/adjustment obtained by treatment with reducing agent.

Scheme 10:

| leuco vat dye sulfuric ester used for coloring | type of hair | further treatment | color result | L a b value* |
|---|---|---|---|---|
| vat violet 1 | Natural blond, coloration | Hydrogen peroxide 9%, pH = 9 | Bright and deeply intense, warm violet | L = 11.14 a = 43.53 b = −27.54 |
| vat violet 1 | Natural blond, after adjustment procedure | Urea, NaOH, hydroxyacetone, pH = 11.5 | Dull, brassy violet | L = 14.83 a = 40.56 b = −9.04 |
| vat yellow 4 | Natural blond, coloration | Hydrogen peroxide 9%, pH = 9 | Bright and glossy straw yellow | L = 57.23 a = 21.37 b = 92.50 |
| vat yellow 4 | Natural blond, after adjustment procedure | Urea, NaOH, hydroxyacetone, pH = 11.5 | Less glossy and intense straw yellow | L = 75.48 a = 11.69 b = 68.03 |

*Color difference is measured via standard L a b values:
L = being a measure of lightness and intensity. Range: 0 = black, 100 = white
a = being a measure of red and green tones. Red = positive values, Green = negative values
b = being a measure of blue and yellow tones. Yellow = positive values, Blue = negative values G Procedure for Correcting a Brassy Color Hue The following table (scheme 11) summarizes the observed color correction/adjustment obtained using solubilized vat blue 4.

Scheme 11:

| leuco vat dye sulfuric ester used for correction | type of hair | oxidation treatment | color result | L a b value* |
|---|---|---|---|---|
| [Reference: bleached brassy hair switch, without dye] | Natural brown 5/0 | Hydrogen peroxide 12% plus Blondor powder **, ratio 1:1 | brassy orange yellow light blond | L = 52.44 a = 13.88 b = 44.61 |
| vat blue 4 120 mg dye 15 mL water 2 g urea | Natural brown 5/0 | Hydrogen peroxide 12% plus Blondor powder **, ratio 1:1 | medium blonde | L = 25.76 a = 13.32 b = 38.21 |
| vat blue 4 40 mg dye 15 ml water 2 g urea | Natural brown 5/0 | Hydrogen peroxide 12% plus Blondor powder **, ratio 1:1 | light beige blond | L = 44.37 a = 9.13 b = 35.45 |

*Color difference is measured via standard L a b values:
L = being a measure of lightness and intensity. Range: 0 = black, 100 = white
a = being a measure of red and green tones. Red = positive values, Green = negative values
b = being a measure of blue and yellow tones. Yellow = positive values, Blue = negative values
**Blondor = bleaching powder, comprising peroxodisulfates, commercial brand of the Wella Company ("Wella Professionals")

The following statements further illustrate the present invention.

1. A method for coloring a keratinous substrate, comprising:
   a1 applying a composition A to said keratinous substrate, said composition A comprising an aqueous medium and a solubilized vat dye dissolved in said medium, wherein said solubilized vat dye is a leuco vat dye sulfuric ester, and wherein composition A is essentially free of oxidative dye precursors selected from primary intermediates and couplers,
   b1 applying a composition B to said keratinous substrate, said composition B having a pH in the range of 3.0-5.0.
2. The method according to statement 1, wherein composition A is essentially free of reducing agents capable of forming an enediol.
3. The method according to statement 1, wherein composition A is essentially free of reducing agents.
4. The method according to statement 1, wherein composition A further comprises a reducing agent selected from sulfites, pyrosulfites, dithionites, thiosulfates, or a combination thereof.
5. The method according to any of the preceding statements, wherein composition A is essentially free of sulfur-containing nucleophiles.
6. The method according to any of the preceding statements, wherein composition A is essentially free of an at least bifunctional Brönsted base of the general formula X—R—Y, wherein X and Y are proton-accepting groups, and R is an organic moiety comprising 1-20 carbon atoms, 0-5 oxygen atoms and 0-5 nitrogen atoms, the at least bifunctional Brönsted base of the general formula X—R—Y having a molecular mass below 500 g/mol.
7. The method according to any of the preceding statements, wherein composition A is essentially free of diamines, aromatic amines, aromatic phenols, or a combination thereof.
8. The method according to any of the preceding statements, wherein composition A is essentially free of pigments, parabens, silicones, or a combination thereof.
9. The method according to any of the preceding statements, wherein composition A comprises two or more solubilized vat dyes.
10. The method according to any of the preceding statements, wherein said solubilized vat dye in composition A is selected from anthracene dyes, anthraquinone dyes, naphthalene dyes, violanthrone dyes, tetraaza-violanthrone dyes, acridine dyes, pyrene dyes, dibenzo[a,h]pyrenes, perylene dyes, terrylene dyes, quaterrylene dyes, or a combination thereof.

11 The method according to any of the preceding statements, wherein said solubilized vat dye in composition A is selected from anthracene dyes, naphthalene dyes, violanthrone dyes, tetraaza-violanthrone dyes, acridine dyes, pyrene dyes, dibenzo[a,h]pyrenes, perylene dyes, terrylene dyes, quaterrylene dyes, or a combination thereof.

12 The method according to any of the preceding statements, wherein said solubilized vat dye in composition A is selected from naphthalene dyes, violanthrone dyes, tetraaza-violanthrone dyes, acridine dyes, perylene dyes, terrylene dyes, quaterrylene dyes, or a combination thereof.

13 The method according to any of the preceding statements, wherein said solubilized vat dye in composition A is selected from naphthalene dyes, tetraaza-violanthrone dyes, acridine dyes, perylene dyes, or a combination thereof.

14 The method according to any of the preceding statements, wherein said solubilized vat dye in composition A is selected from solubilized vat blue 4 (CAS #747-19-5), solubilized vat violet 1 (CAS #1324-57-8), solubilized vat yellow 4 (CAS #3564-70-3), solubilized vat green 1 (CAS #2538-84-3), solubilized vat yellow 1 (CAS #6487-09-8), solubilize vat red 34 (CAS #12226-70-9), solubilized vat red 10 (CAS #10126-90-6), solubilized vat orange 9 (CAS #70356-06-8), solubilized vat orange 3 (CAS #10290-03-6), solubilized vat blue 6 (CAS #2519-28-0), solubilized vat yellow 7 (CAS #3956-62-5), solubilized vat brown 1 (CAS #23725-15-7), solubilized vat blue 20, or a combination thereof.

15 The method according to any of statements 1-13, wherein said solubilized vat dye in composition A is selected from solubilized vat violet 1 (CAS #1324-57-8), solubilized vat green 1 (CAS #2538-84-3), solubilized vat yellow 1 (CAS #6487-09-8), solubilize vat red 34 (CAS #12226-70-9), solubilized vat orange 9 (CAS #70356-06-8), solubilized vat orange 3 (CAS #10290-03-6), solubilized vat blue 20, or a combination thereof.

16 The method according to any of the preceding statements, wherein composition A comprises a solubilized vat dye according to any one of Formulae (I)-(X):

solubilized Pigment Violet 19 according to formula (I):

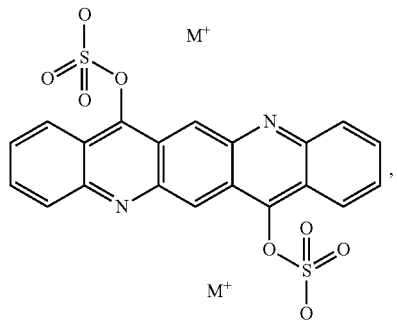

(I)

solubilized Pigment Red 122 according to formula (II):

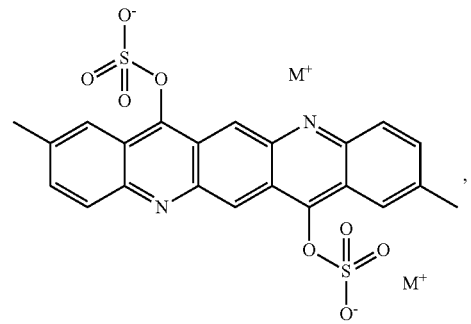

(II)

solubilized Pigment Red 194 according to formula (III):

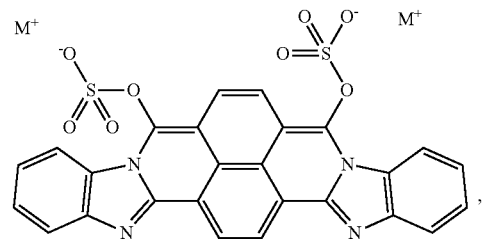

(III)

solubilized Pigment Orange 43 according to formula (IV):

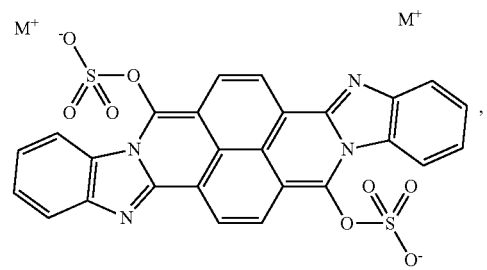

(IV)

solubilized tetraazaviolanthron-trans-black according to formula (V):

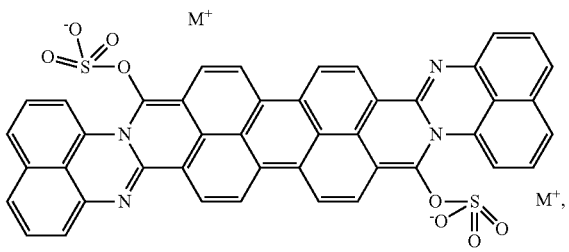

(V)

solubilized tetraazaviolanthron-cis-black according to formula (VI):

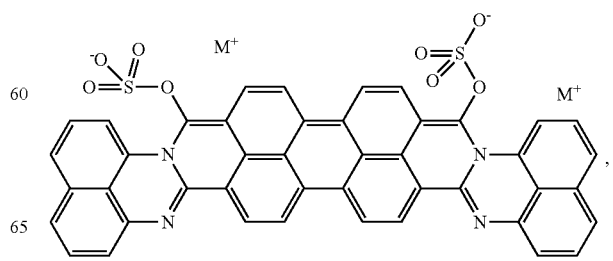

(VI)

-continued solubilized perylene-amidine-trans-blue according to formula (VII):

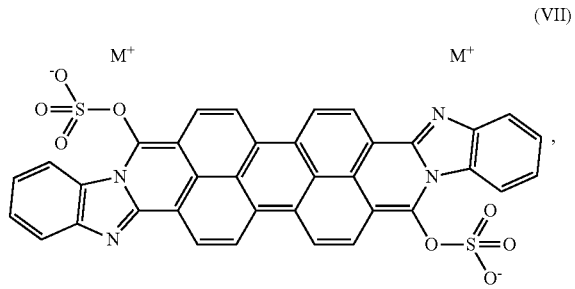

(VII)

solubilized perylene-amidine-cis-blue according to formula (VIII):

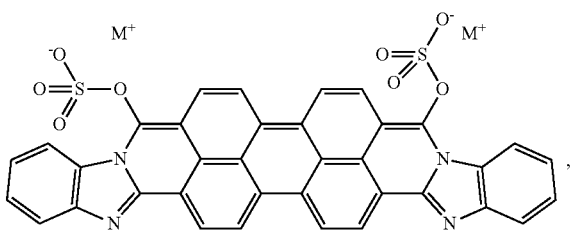

(VIII)

solubilized naphthaline-amidine-trans-blue according to formula (IX):

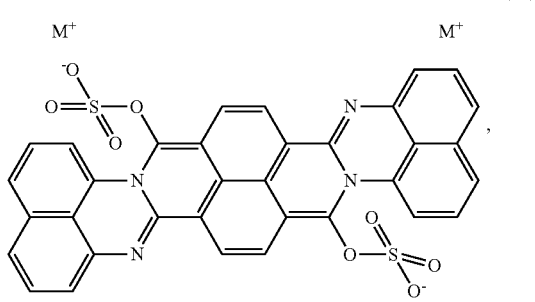

(IX)

solubilized naphthaline-amidine-cis-blue according to formula (X):

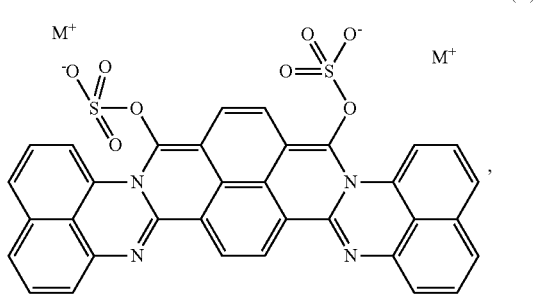

(X)

or a combination thereof.

17 The method according to any of the preceding statements, wherein composition A has a pH in the range of 8.0-10.0, in particular a pH in the range of 8.5-9.5.

18 The method according to any of the preceding statements, wherein composition A further comprises a penetration enhancer.

19 The method according to statement 18, wherein said penetration enhancer is selected from ammonia, urea, monoethanolamine, or a combination thereof.

20 The method according to any of the preceding statements, wherein composition A further comprises one or more components selected from pH adjusters, chelating agents, direct dyes, fragrances, care components, texture ingredients, medium reagents, solvents, surfactants.

21 The method according to any of the preceding statements, wherein composition B has a pH in the range of 3.2-4.0, such as a pH of about 3.5.

22 The method according to any of the preceding statements, wherein composition B comprises a monofunctional organic or inorganic acid.

23 The method according to any of statements 1-21, wherein composition B comprises an acid selected from acetic acid, boric acid, citric acid, tartaric acid, malic acid, maleic acid, fumaric acid, or a combination thereof, in particular wherein composition B comprises citric acid, malic acid, or a combination thereof.

24 The method according to any of the preceding statements, further comprising:
c applying a composition C to said keratinous substrate, said composition C comprising an oxidizing agent.

25 The method according to statement 24, wherein composition C has a pH of in the range of 8.0-11.0, in particular in the range of 8.5-9.5, such as a pH of about 9.0.

26 The method according to statement 24 or 25, wherein the oxidizing agent in composition C comprises a peroxide, in particular hydrogen peroxide.

27 The method according to any of statements 24-26, wherein the oxidizing agent in composition C comprises a persulfate and/or a percarbonate.

28 The method according to any of statements 24-27, wherein composition C further comprises a bleaching enhancer.

29 The method according to any of the preceding statements, wherein the keratinous substrate is mammalian hair, in particular human scalp.

30 The method according to statement 29, further comprising styling the hair.

31 The method according to statement 30, wherein styling the hair comprises perming or straightening the hair.

32 The method according to any of statements 29-31, further comprising shampooing, conditioning, post-treating and/or drying the hair.

33 A method for correcting a brassy color shade or hue of mammalian hair, comprising:
a2 applying a composition AA to the hair, said composition AA comprising an aqueous medium and a solubilized vat dye dissolved in said medium, wherein said solubilized vat dye is a leuco vat dye sulfuric ester, and wherein composition AA is essentially free of oxidative dye precursors selected from primary intermediates and couplers,
b2 applying a composition BB to the hair, said composition BB having a pH in the range of 3.0-5.0.

34 The method according to statement 33, wherein composition AA is essentially free of reducing agents capable of forming an enediol.

35 The method according to statement 33, wherein composition AA is essentially free of reducing agents.

36 The method according to statement 33, wherein composition AA further comprises a reducing agent selected from sulfites, pyrosulfites, dithionites, thiosulfates, or a combination thereof.

37 The method according to any of statements 33-36, wherein composition AA is essentially free of sulfur-containing nucleophiles.

38 The method according to any of statements 33-37, wherein composition AA is essentially free of an at least bifunctional Brönsted base of the general formula X—R—Y, wherein X and Y are proton-accepting groups, and R is an organic moiety comprising 1-20 carbon atoms, 0-5 oxygen atoms and 0-5 nitrogen atoms, the at least bifunctional Brönsted base of the general formula X—R—Y having a molecular mass below 500 g/mol.

39 The method according to any of statements 33-38, wherein composition AA is essentially free of diamines, aromatic amines, aromatic phenols, or a combination thereof.

40 The method according to any of statements 33-39, wherein composition AA is essentially free of pigments, parabens, silicones, or a combination thereof.

41 The method according to any of statements 33-40, wherein composition AA comprises two or more solubilized vat dyes.

42 The method according to any of statements 33-41, wherein said solubilized vat dye(s) in composition AA is/are derived from a vat dye or combination of vat dyes giving overall a blue or bluish color.

43 The method according to any of statements 33-42, wherein said solubilized vat dye in composition AA is selected from solubilized vat blue 4 (CAS #747-19-5), solubilized vat blue 6 (CAS #2519-28-0), solubilized vat blue 20, solubilized perylene-amidine-trans-blue according to Formula (VII):

(VII)

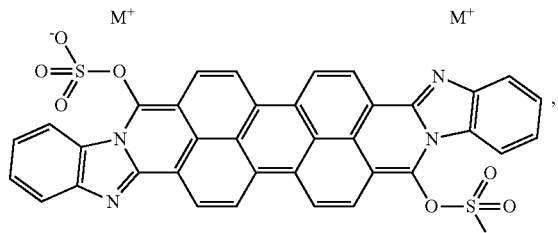

solubilized perylene-amidine-cis-blue according to Formula (VIII):

(VIII)

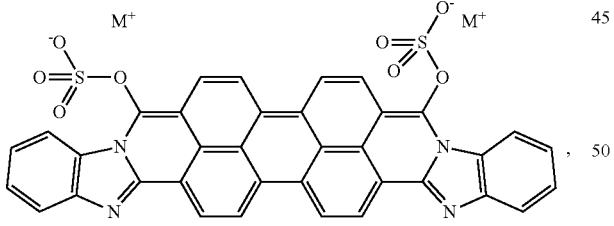

solubilized naphthaline-amidine-trans-blue according to Formula (IX):

(IX)

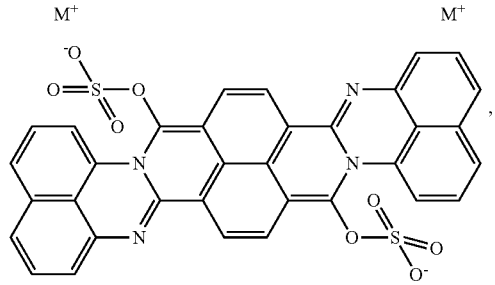

-continued
solubilized naphthaline-amidine-cis-blue according to Formula (X):

(X)

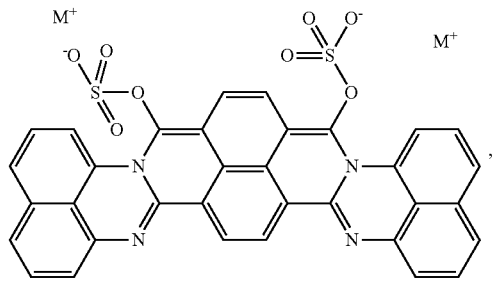

or a combination thereof.

44 The method according to any of statements 33-43, wherein composition AA has a pH in the range of 8.0-10.0, in particular a pH in the range of 8.5-9.5.

45 The method according to any of statements 33-44, wherein composition AA further comprises a penetration enhancer.

46 The method according to statement 45, wherein said penetration enhancer is selected from ammonia, urea, monoethanolamine, or a combination thereof.

47 The method according to any of statements 33-46, wherein composition AA further comprises one or more components selected from pH adjusters, chelating agents, direct dyes, fragrances, care components, texture ingredients, medium reagents, solvents, surfactants.

48 The method according to any of statements 33-47, wherein composition BB has a pH in the range of 3.2-4.0, such as a pH of about 3.5.

49 The method according to any of statements 33-48, wherein composition BB comprises a monofunctional organic or inorganic acid.

50 The method according to any of statements 33-49, wherein composition BB comprises an acid selected from acetic acid, boric acid, citric acid, tartaric acid, malic acid, maleic acid, fumaric acid, or a combination thereof, in particular wherein composition B comprises citric acid, malic acid, or a combination thereof.

51 The method according to any of statements 33-50, further comprising:
c2 applying a composition CC to said keratinous substrate, said composition CC comprising an oxidizing agent.

52 The method according to statement 51, wherein composition CC has a pH of in the range of 8.0-11.0, in particular in the range of 8.5-9.5, such as a pH of about 9.0.

53 The method according to statement 51 or 52, wherein the oxidizing agent in composition CC comprises a peroxide, in particular hydrogen peroxide.

54 The method according to any of statements 33-53, wherein the mammalian hair is lifted mammalian hair.

55 The method according to statement 54, wherein the lifted mammalian hair is bleached mammalian hair.

56 The method according to any of statements 33-55, wherein the mammalian hair is human scalp.

57 The method according to any of statements 33-56, further comprising styling the hair.

58 The method according to statement 57, wherein styling the hair comprises perming or straightening the hair.

59 The method according to any of statements 33-58, further comprising shampooing, conditioning, post-treating and/or drying the hair.

60 A method for changing the color of a vat-dye-colored keratinous substrate, comprising applying to the keratinous substrate a composition D having a pH in the range of 11.0-12.0, composition D further comprising a reducing agent.

61 The method according to statement 61, wherein the reducing agent is selected from monohydroxy acetone, dihydroxy acetone, 3-hydroxy-2-butanone, 2-hydroxy-cyclohexane-1-one, glycolaldehyde, 2-hydroxy-1,2-diphenylethan-1-one, 1,5-dihydroxy-pentan-2-one, 2,3-dihydroxy-acrylaldehyde, 2,3-dihydroxy-cyclopentan-1-one, or a combination thereof.

62 A composition for coloring a keratinous substrate, comprising an aqueous medium and a solubilized vat dye dissolved in said medium, wherein said solubilized vat dye is a leuco vat dye sulfuric ester, said vat dye selected from anthracene dyes, anthraquinone dyes, naphthalene dyes, violanthrone dyes, tetraaza-violanthrone dyes, acridine dyes, pyrene dyes, dibenzo[a,h]pyrenes, perylene dyes, terrylene dyes, quaterrylene dyes, wherein said composition is essentially free of oxidative dye precursors selected from primary intermediates and couplers, wherein said composition is essentially free of reducing agents capable of forming an enediol, and wherein said composition is essentially free of sulfur-containing nucleophiles.

63 The composition according to statement 62, wherein the composition is essentially free of reducing agents.

64 The composition according to statement 62, wherein the composition further comprises a reducing agent selected from sulfites, pyrosulfites, dithionites, thiosulfates, or a combination thereof.

65 The composition according to any of statements 62-64, wherein the composition is essentially free of an at least bifunctional Brönsted base of the general formula X—R—Y, wherein X and Y are proton-accepting groups, and R is an organic moiety comprising 1-20 carbon atoms, 0-5 oxygen atoms and 0-5 nitrogen atoms, the at least bifunctional Brönsted base of the general formula X—R—Y having a molecular mass below 500 g/mol.

66 The composition according to any of statements 62-65, wherein the composition is essentially free of diamines, aromatic amines, aromatic phenols, or a combination thereof.

67 The composition according to any of statements 62-66, wherein the composition is essentially free of pigments, parabens, silicones, or a combination thereof.

68 The composition according to any of statements 62-67, comprising two or more leuco vat dye sulfuric esters.

69 The composition according to any of statements 62-68, wherein said vat dye is selected from anthracene dyes, naphthalene dyes, violanthrone dyes, tetraaza-violanthrone dyes, acridine dyes, pyrene dyes, dibenzo[a,h]pyrenes, perylene dyes, terrylene dyes, quaterrylene dyes, or a combination thereof.

70 The composition according to any of statements 62-69, wherein said vat dye is selected from naphthalene dyes, violanthrone dyes, tetraaza-violanthrone dyes, acridine dyes, perylene dyes, terrylene dyes, quaterrylene dyes, or a combination thereof.

71 The composition according to any of statements 62-70, wherein said vat dye is selected from naphthalene dyes, tetraaza-violanthrone dyes, acridine dyes, perylene dyes, or a combination thereof.

72 The composition according to any of statements 62-71, wherein said solubilized vat dye is selected from solubilized vat blue 4 (CAS #747-19-5), solubilized vat violet 1 (CAS #1324-57-8), solubilized vat yellow 4 (CAS #3564-70-3), solubilized vat green 1 (CAS #2538-84-3), solubilized vat yellow 1 (CAS #6487-09-8), solubilize vat red 34 (CAS #12226-70-9), solubilized vat red 10 (CAS #10126-90-6), solubilized vat orange 9 (CAS #70356-06-8), solubilized vat orange 3 (CAS #10290-03-6), solubilized vat blue 6 (CAS #2519-28-0), solubilized vat yellow 7 (CAS #3956-62-5), solubilized vat brown 1 (CAS #23725-15-7), solubilized vat blue 20, or a combination thereof.

73 The composition according to any of statements 62-71, wherein said solubilized vat dye is selected from solubilized vat violet 1 (CAS #1324-57-8), solubilized vat green 1 (CAS #2538-84-3), solubilized vat yellow 1 (CAS #6487-09-8), solubilize vat red 34 (CAS #12226-70-9), solubilized vat orange 9 (CAS #70356-06-8), solubilized vat orange 3 (CAS #10290-03-6), solubilized vat blue 20, or a combination thereof.

74 The composition according to any of statements 62-73, comprising a solubilized vat dye according to any one of Formulae (I)-(X):

solubilized Pigment Violet 19 according to formula (I):

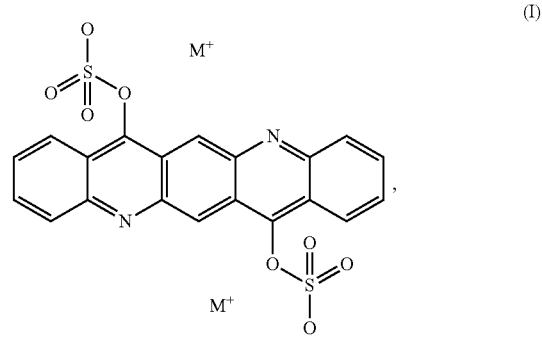

solubilized Pigment Red 122 according to formula (II):

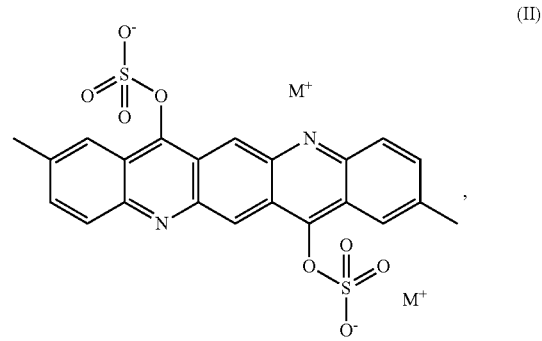

solubilized Pigment Red 194 according to formula (III):

(III)

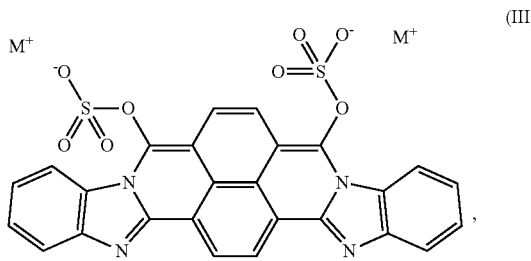

solubilized Pigment Orange 43 according to formula (IV):

(IV)

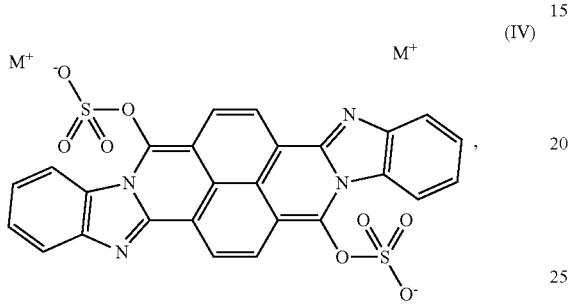

solubilized tetraazaviolanthron-trans-black according to formula (V):

(V)

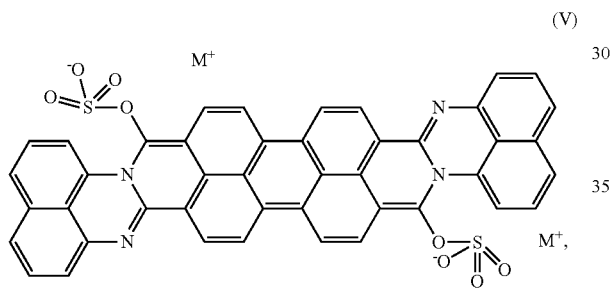

solubilized tetraazaviolanthron-cis-black according to formula (VI):

(VI)

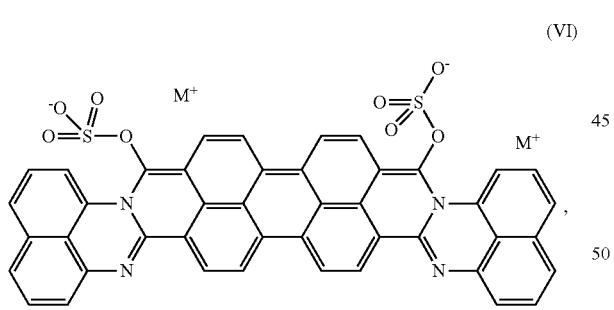

solubilized perylene-amidine-trans-blue according to formula (VII):

(VII)

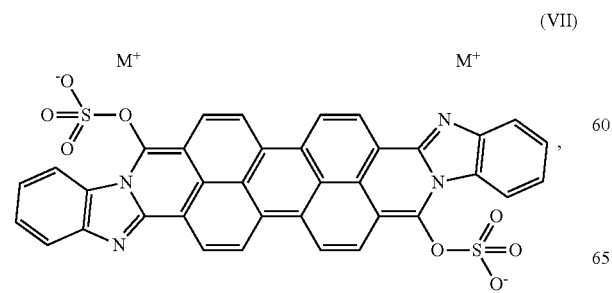

solubilized perylene-amidine-cis-blue according to formula (VIII):

(VIII)

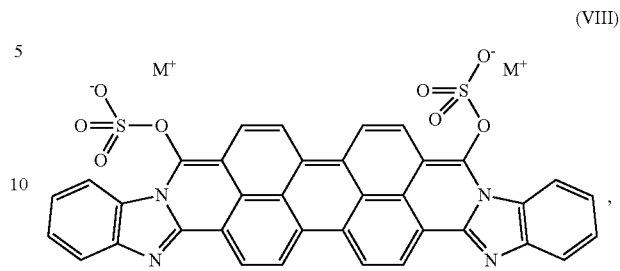

solubilized naphthaline-amidine-trans-blue according to formula (IX):

(IX)

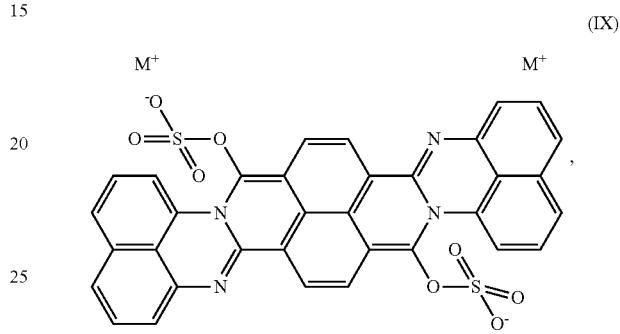

solubilized naphthaline-amidine-cis-blue according to formula (X):

(X)

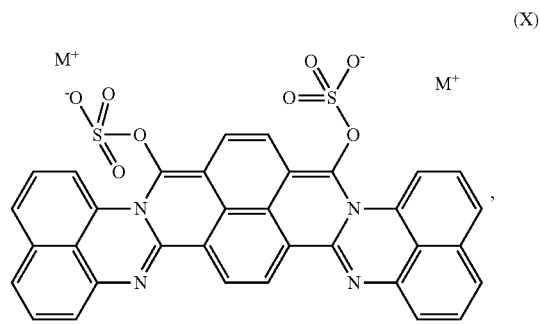

or a combination thereof.

75 The composition according to any of statements 62-71, wherein said solubilized vat dye(s) is/are derived from a vat dye or combination of vat dyes giving overall a blue or bluish color, in particular wherein said solubilized vat dye is a solubilized blue vat dye selected from solubilized vat blue 4 (CAS #747-19-5), solubilized vat blue 6 (CAS #2519-28-0), solubilized vat blue 20, solubilized perylene-amidine-trans-blue according to Formula (VII):

(VII)

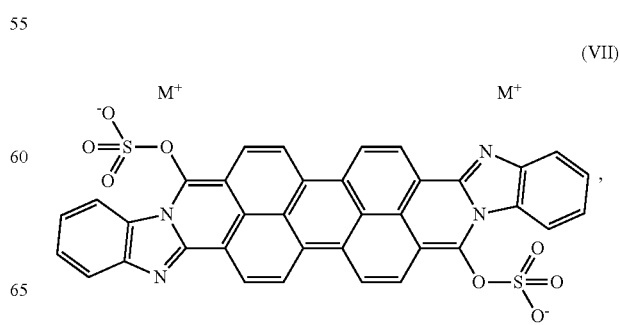

-continued solubilized perylene-amidine-cis-blue according to Formula (VIII):

(VIII)

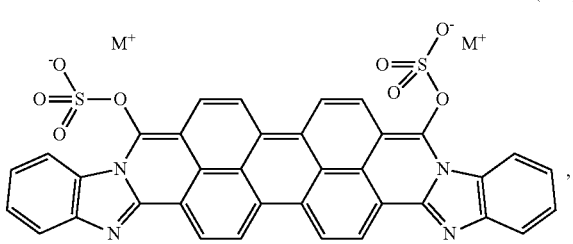

solubilized naphthaline-amidine-trans-blue according to Formula (IX):

(IX)

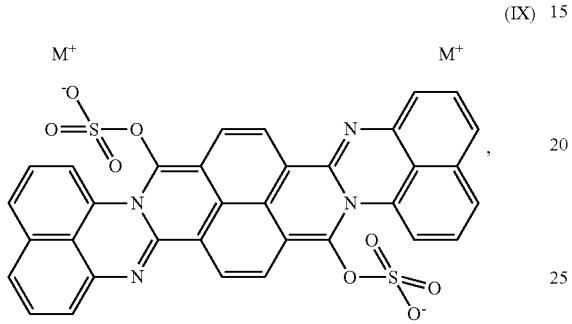

solubilized naphthaline-amidine-cis-blue according to Formula (X):

(X)

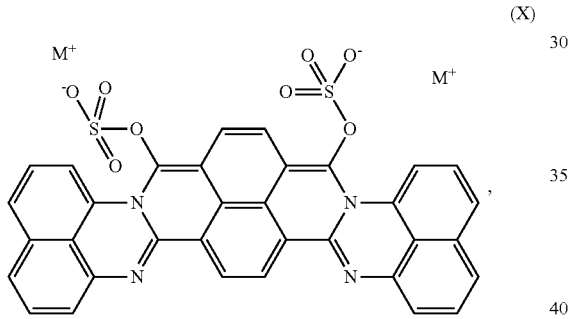

or a combination thereof.

76 The composition according to any of statements 62-75, wherein the composition has a pH of from 8.0-10.0, in particular a pH of from 8.5-9.5.

77 The composition according to any of statements 62-76, wherein the composition further comprises a penetration enhancer, in particular a penetration enhancer selected from ammonia, urea, monoethanolamine, or a combination thereof.

78 The composition according to any of statements 62-77, wherein the composition further comprises one or more components selected from pH adjusters, chelating agents, direct dyes, fragrances, care components, texture ingredients, medium reagents, solvents, surfactants.

79 The composition according to any of statements 62-78, wherein the keratinous substrate is mammalian hair, in particular human scalp.

80 A kit for coloring a keratinous substrate, comprising:
a compartment A comprising a leuco vat dye sulfuric ester or salt thereof,
a compartment B comprising an acid or salt thereof.

81 The kit according to statement 80, wherein compartment A comprises a mixture of two or more leuco vat dye sulfuric esters or salts thereof.

82 The kit according to statement 80 or 81, wherein compartment B comprises a monofunctional organic or inorganic acid.

83 The kit according to statement 80 or 81, wherein compartment B comprises an acid selected from acetic acid, boric acid, citric acid, tartaric acid, malic acid, maleic acid, fumaric acid, or a combination thereof, in particular wherein composition B comprises citric acid, malic acid, or a combination thereof.

84 The kit according to any of statements 81-83, further comprising a compartment C comprising an oxidizing agent.

85 The kit according to statement 84, wherein compartment C comprises a peroxide, in particular hydrogen peroxide.

86 The kit according to statement 84 or 85, wherein compartment C comprises a persulfate and/or a percarbonate.

87 The kit according to any of statements 83-86, the kit further comprising a bleaching enhancer.

88 The kit according to any of statements 80-87, further comprising a compartment D comprising a reducing agent.

89 The kit according to statement 88, wherein the reducing agent is selected from monohydroxy acetone, dihydroxy acetone, 3-hydroxy-2-butanone, 2-hydroxycyclohexane-1-one, glycolaldehyde, 2-hydroxy-1,2-diphenylethan-1-one, 1,5-dihydroxy-pentan-2-one, 2,3-dihydroxy-acrylaldehyde, 2,3-dihydroxy-cyclopentan-1-one, or a combination thereof.

90 The kit according to any of statement 80-89, wherein the content of compartment A and/or compartment B and/or compartment C and/or compartment D is present in solid form or in semi-solid form or in liquid form.

91 The kit according to any of statement 80-90, further comprising:
a compartment comprising a medium which upon mixing with the contents of compartment A is capable of forming composition A used in step (a) of statement 1,
a compartment comprising a medium which upon mixing with the contents of compartment B is capable of forming composition B used in step (b) of statement 1,
a compartment comprising a medium which upon mixing with the contents of compartment C is capable of forming composition C used in step (c) of statement 1, and/or
a compartment comprising a medium which upon mixing with the contents of compartment D is capable of forming composition D used in statement 61.

92 The kit according to any of statement 80-91, further comprising at least one compartment comprising one or more leuco vat dye sulfuric esters, or salts thereof, resulting overall in a color different from the one provided by the leuco vat dye sulfuric ester(s) in compartment A.

Solubilized Pigment Violet 19 according to formula (I):

(I)
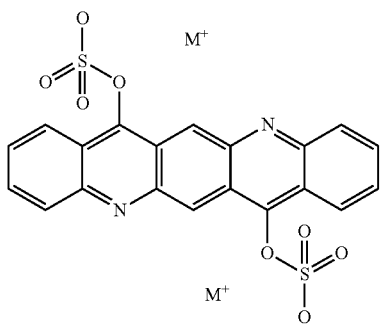

Solubilized Pigment Red 122 according to formula (II):

(II)
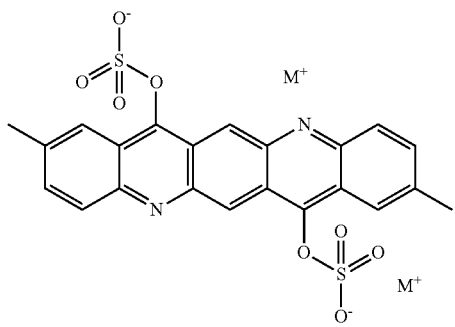

Solubilized Pigment Red 194 according to formula (III):

(III)
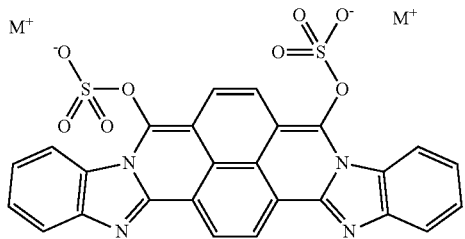

Solubilized Pigment Orange 43 according to formula (IV):

(IV)
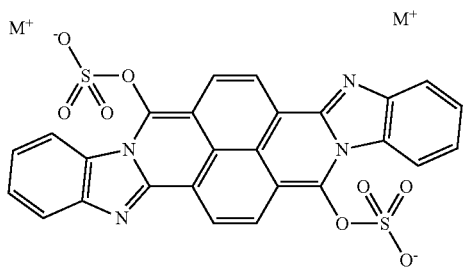

Solubilized tetraazaviolanthron-trans-black according to formula (V):

(V)
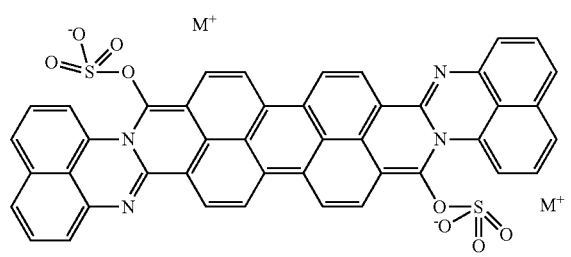

Solubilized tetraazaviolanthron-cis-black according to formula (VI):

(VI)
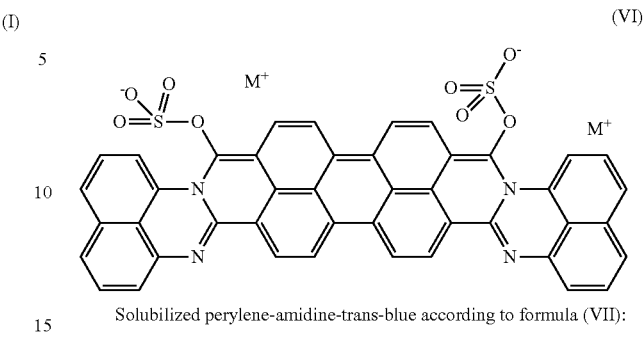

Solubilized perylene-amidine-trans-blue according to formula (VII):

(VII)
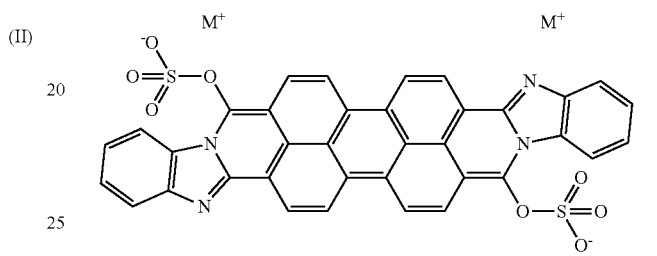

Solubilized perylene-amidine-cis-blue according to formula (VIII):

(VIII)
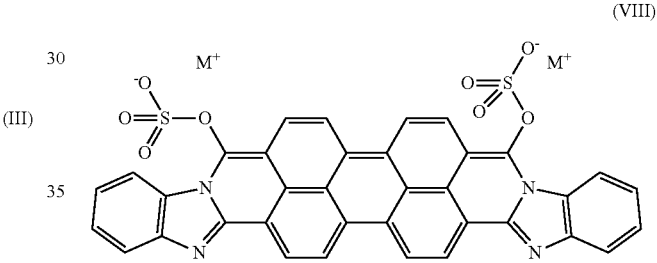

Solubilized naphthaline-amidine-trans-blue according to formula (IX):

(IX)
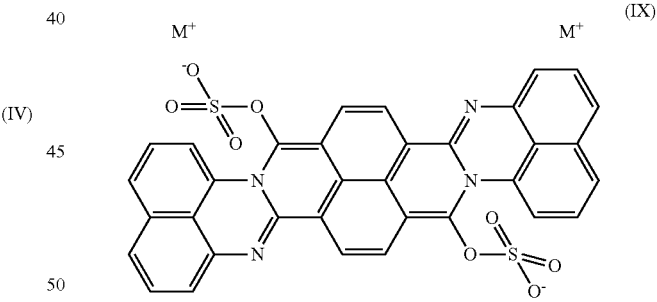

Solubilized naphthaline-amidine-cis-blue according to formula (X):

(X)
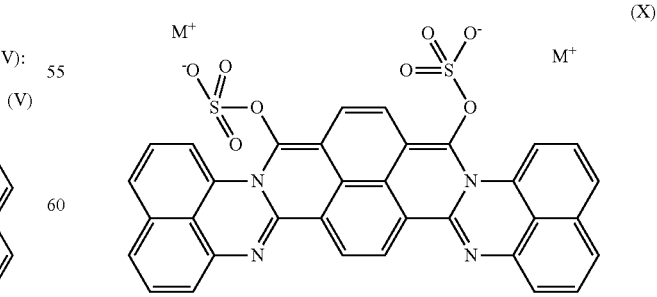

103 Use of a leuco vat dye sulfuric ester according to any of statements 93-102 in a vat dyeing process.

104 Use of a leuco vat dye sulfuric ester according to any of statements 93-102 for coloring a keratinous substrate.

105 Use of a leuco vat dye sulfuric ester according to any of statements 93-102 for coloring mammalian hair, in particular human scalp.

106 A substrate having adsorbed thereto a leuco vat dye sulfuric ester according to any of statements 93-102.

107 The substrate according to statement 106, wherein the substrate is a fiber.

108 The substrate according to statement 106 or 107, wherein the substrate is a keratinous substrate.

109 The substrate according to any of statements 106-108, wherein the substrate is mammalian hair.

110 The substrate according to statement 109, wherein the substrate is human scalp.

111 The substrate according to statement 109, wherein the substrate is selected from wool and silk.

112 The substrate according to statement 106 or 107, wherein the substrate is a cellulosic substrate.

113 The substrate according to statement 112, wherein the substrate is selected from natural and manufactured cellulosic fibers.

What is claimed is:

1. A method for coloring a keratinous substrate, comprising:
   a1. applying a composition A to said keratinous substrate, said composition A comprising an aqueous medium and a solubilized vat dye dissolved in said medium, wherein said solubilized vat dye is a leuco vat dye sulfuric ester, and wherein composition A is essentially free of oxidative dye precursors selected from primary intermediates and couplers,
   b1. applying a composition B to said keratinous substrate, said composition B having a pH in the range of 3.0-5.0.

2. The method according to claim 1, wherein composition A is essentially free of reducing agents capable of forming an enediol and/or wherein composition A is essentially free of sulfur-containing nucleophiles.

3. The method according to claim 1, wherein composition A is essentially free of diamines, aromatic amines, aromatic phenols, pigments, parabens, silicones, or a combination thereof.

4. The method according to claim 1, wherein composition A comprises two or more solubilized vat dyes.

5. The method according to claim 1, wherein said solubilized vat dye in composition A is selected from anthracene dyes, anthraquinone dyes, naphthalene dyes, violanthrone dyes, tetraaza-violanthrone dyes, acridine dyes, pyrene dyes, dibenzo[a,h]pyrenes, perylene dyes, terrylene dyes, quaterrylene dyes, or a combination thereof.

6. The method according to claim 1, wherein composition A has a pH in the range of 8.0-10.0.

7. The method according to claim 1, wherein composition A further comprises a penetration enhancer.

8. The method according to claim 1, wherein composition B has a pH in the range of 3.2-4.0.

9. The method according to claim 1, further comprising:
   c. applying a composition C to said keratinous substrate, said composition C comprising an oxidizing agent.

10. The method according to claim 9, wherein composition C has a pH of in the range of 8.0-11.0.

11. The method according to claim 9, wherein the oxidizing agent in composition C comprises a peroxide, a persulfate, a percarbonate, or a combination thereof.

12. The method according to claim 1, wherein the keratinous substrate is mammalian hair.

13. A method for correcting a brassy color shade or hue of mammalian hair, comprising:
   a2. applying a composition AA to the hair, said composition AA comprising an aqueous medium and a solubilized vat dye dissolved in said medium, wherein said solubilized vat dye is a leuco vat dye sulfuric ester, and wherein composition AA is essentially free of oxidative dye precursors selected from primary intermediates and couplers,
   b2. applying a composition BB to the hair, said composition BB having a pH in the range of 3.0-5.0.

14. The method according to claim 13, wherein composition AA comprises two or more solubilized vat dyes.

15. The method according to claim 13, wherein said solubilized vat dye(s) in composition AA is/are derived from a vat dye or combination of vat dyes giving overall a blue or bluish color.

16. The method according to claim 13, wherein composition AA has a pH in the range of 8.0-10.0.

17. The method according to claim 13, wherein composition BB has a pH in the range of 3.2-4.0.

18. The method according to claim 13, further comprising:
   c2. applying a composition CC to said keratinous substrate, said composition CC comprising an oxidizing agent.

19. The method according to claim 18, wherein composition CC has a pH of in the range of 8.0-11.0.

20. A composition for coloring a keratinous substrate, comprising an aqueous medium and a solubilized vat dye dissolved in said medium, wherein said solubilized vat dye is a leuco vat dye sulfuric ester, said vat dye selected from anthracene dyes, anthraquinone dyes, naphthalene dyes, violanthrone dyes, tetraaza-violanthrone dyes, acridine dyes, pyrene dyes, dibenzo[a,h]pyrenes, perylene dyes, terrylene dyes, quaterrylene dyes, wherein said composition is essentially free of oxidative dye precursors selected from primary intermediates and couplers, wherein said composition is essentially free of reducing agents capable of forming an enediol, and wherein said composition is essentially free of sulfur-containing nucleophiles.

21. The composition according to claim 20, wherein the composition is essentially free of diamines, aromatic amines, aromatic phenols, pigments, parabens, silicones, or a combination thereof.

22. The composition according to claim 20, comprising two or more leuco vat dye sulfuric esters.

23. The composition according to claim 20, wherein said solubilized vat dye(s) is/are derived from a vat dye or combination of vat dyes giving overall a blue or bluish color.

24. The composition according to claim 20, wherein the composition has a pH of from 8.0-10.0.

* * * * *